United States Patent
Nakamura

(10) Patent No.: US 10,426,568 B2
(45) Date of Patent: Oct. 1, 2019

(54) PROJECTION SYSTEM

(71) Applicant: Panasonic Intellectual Property Management Co., Ltd., Osaka (JP)

(72) Inventor: Masaaki Nakamura, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 277 days.

(21) Appl. No.: 15/375,783

(22) Filed: Dec. 12, 2016

(65) Prior Publication Data

US 2017/0086940 A1 Mar. 30, 2017

Related U.S. Application Data

(63) Continuation of application No. PCT/JP2015/003101, filed on Jun. 22, 2015.

(30) Foreign Application Priority Data

Jun. 25, 2014 (JP) .................. 2014-130004

(51) Int. Cl.
*A61B 90/00* (2016.01)
*A61B 10/00* (2006.01)
(Continued)

(52) U.S. Cl.
CPC ............ *A61B 90/36* (2016.02); *A61B 5/0071* (2013.01); *A61B 10/00* (2013.01); *A61B 90/00* (2016.02);
(Continued)

(58) Field of Classification Search
CPC .............................. A61B 90/36; A61B 5/0071
See application file for complete search history.

(56) References Cited

U.S. PATENT DOCUMENTS 5,772,593 A 6/1998 Hakamata
5,969,754 A * 10/1999 Zeman ................. G09B 21/008
348/136

(Continued)

FOREIGN PATENT DOCUMENTS

JP 9-024053 1/1997
JP 2008-203491 A 9/2008
(Continued)

OTHER PUBLICATIONS

The Extended European Search Report dated May 31, 2017 for the related European Patent Application No. 15811253.2.
(Continued)

*Primary Examiner* — Rowina J Cattungal
(74) *Attorney, Agent, or Firm* — McDermott Will & Emery LLP

(57) ABSTRACT

The present disclosure provides a more easy-to-use projection system including an imaging unit that captures an image of a specific area, which is specified by light excited by light having a predetermined wavelength, in a subject, a projector that projects an image of the specific area by visible light, a controller that controls such that the image of the specific area and associated information associated with the image of the specific area are projected onto the subject, and an optical unit that causes an optical path of the imaging unit with respect to the subject and an optical path of the projector with respect to the subject to coincide with each other.

11 Claims, 19 Drawing Sheets

(51) Int. Cl.
  *H04N 5/225* (2006.01)
  *H04N 5/33* (2006.01)
  *H04N 7/18* (2006.01)
  *A61B 5/00* (2006.01)
  G03B 15/14 (2006.01)
  G03B 17/54 (2006.01)
  A61B 90/30 (2016.01)

(52) U.S. Cl.
  CPC ............ *H04N 5/2256* (2013.01); *H04N 5/33* (2013.01); *H04N 7/183* (2013.01); *A61B 90/30* (2016.02); *A61B 90/361* (2016.02); *A61B 2090/366* (2016.02); *G03B 15/14* (2013.01); *G03B 17/54* (2013.01)

(56) References Cited

U.S. PATENT DOCUMENTS

| | | |
|---|---|---|
| 2008/0004533 A1 | 1/2008 | Jansen et al. |
| 2011/0164192 A1* | 7/2011 | Ozawa ................... G03B 21/14 348/744 |
| 2011/0184291 A1* | 7/2011 | Okamura ............... A61B 8/483 600/443 |
| 2012/0018637 A1* | 1/2012 | Mitani ................. H03K 17/941 250/339.02 |
| 2012/0209103 A1 | 8/2012 | Sakuragi |
| 2014/0218300 A1* | 8/2014 | Muraki ................. G03B 17/54 345/168 |
| 2015/0198797 A1* | 7/2015 | Andre ................. A61B 5/7425 348/80 |

FOREIGN PATENT DOCUMENTS

| | | |
|---|---|---|
| JP | 2011-172918 | 9/2011 |
| JP | 2012-045198 | 3/2012 |
| JP | 2012-165910 | 9/2012 |
| JP | 2012-521863 | 9/2012 |
| WO | 2010/117806 | 10/2010 |

OTHER PUBLICATIONS

International Search Report of PCT application No. PCT/JP2015/003101 dated Sep. 15, 2015.

* cited by examiner

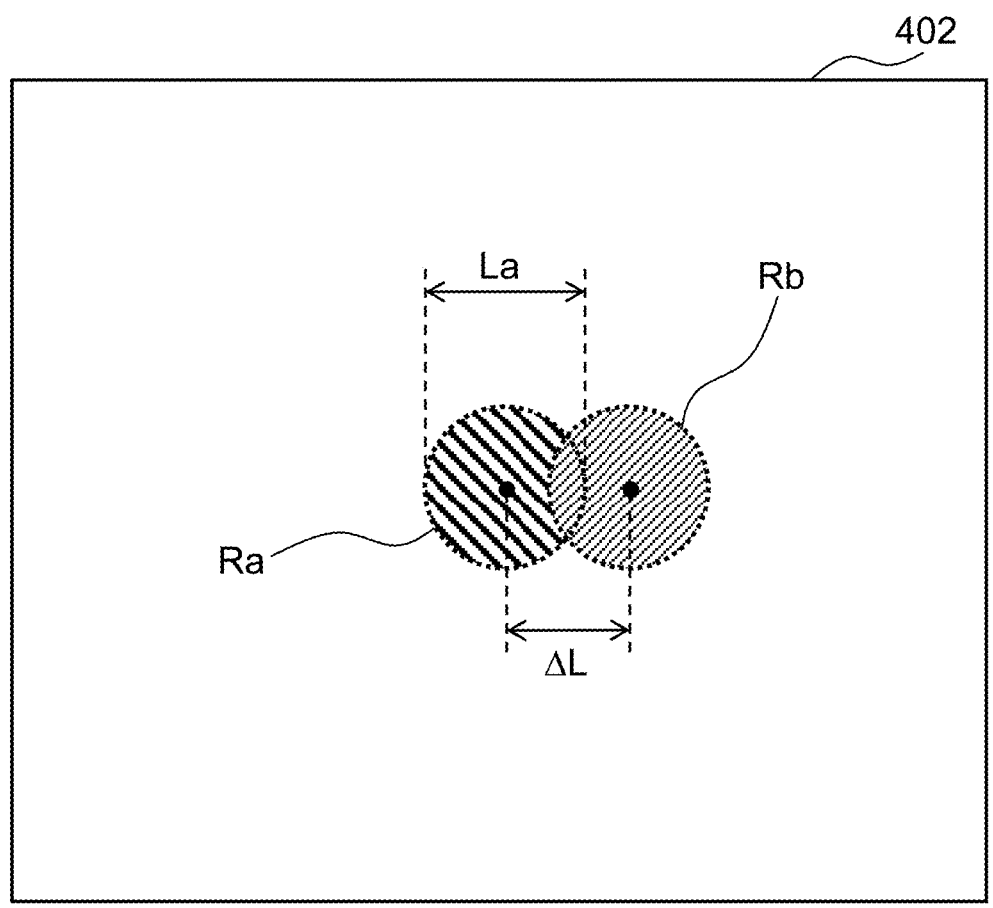

FIG. 9

| Scanning pattern | Characteristic | Scale of illuminance | Illuminance on the irradiated surface ×10,000 Lux (Upon oscillation in 25 lumens) | |
|---|---|---|---|---|
| | | | Maximum 100mm×100mm | Minimum 10mm×10mm |
| Raster scanning | Scanning for only inside | ×1 | 0.25 | 25 |
| Vector scanning | Scanning for only boundary | ×20 | 5 | 500 | ns
PROJECTION SYSTEM

BACKGROUND

1. Technical Field

The present disclosure relates to a projection system that projects an image onto a subject.

2. Description of the Related Art

Patent Literature 1 discloses a surgery supporting system that outputs image data indicating an affected part of a living body, which will undergo surgery, from a fluorescent imaging device, and reproduces an image based on the image data and displays the image on the actual affected part by an image projection apparatus. A substance that emits fluorescence by irradiation of light having a predetermined wavelength is administered in advance to the affected part of the living body. That is, this system supports for confirmation of a lesion by displaying, on the actual affected part, a fluorescent image of the affected part emitting the fluorescence.

CITATION LIST

Patent Literature

PTL 1: Unexamined Japanese Patent Publication No. H09-24053

SUMMARY

The present disclosure provides a projection system including: an imaging unit that captures an image of a specific area, which is specified by light excited by light having a predetermined wavelength, in a subject; a projector that projects the image of the specific area and associated information associated with the image of the specific area by visible light; a distance acquiring unit that acquires a distance from the distance acquiring unit to the subject; a controller that adjusts a projection magnification in the projector based on the distance, acquired by the distance acquiring unit, from the distance acquiring unit to the subject; and an optical unit that causes an optical path of the imaging unit with respect to the subject and an optical path of the projector with respect to the subject to coincide with each other.

BRIEF DESCRIPTION OF THE DRAWINGS

FIG. 6 is a view illustrating the state of projection surface 402 in an example of use of optical adjustment device 400.

FIG. 9 is a diagram for describing scanning patterns by projector 220.

DESCRIPTION OF EMBODIMENTS

Exemplary embodiments will be described below in detail with reference to the drawings as necessary. However, more than necessary detailed descriptions will sometimes be omitted. For example, detailed descriptions for matters which have already been well known in the art and redundant descriptions for substantially the same configurations will sometimes be omitted. This is to prevent the following description from becoming unnecessarily redundant to facilitate understanding of a person skilled in the art.

Note that the accompanying drawings and the following description are provided by the applicant in order for a person skilled in the art to sufficiently understand the present disclosure, and they are not intended to limit the subject matter set forth in the claims.

First Exemplary Embodiment

1. Outline of Surgery Supporting System

Figure 1:
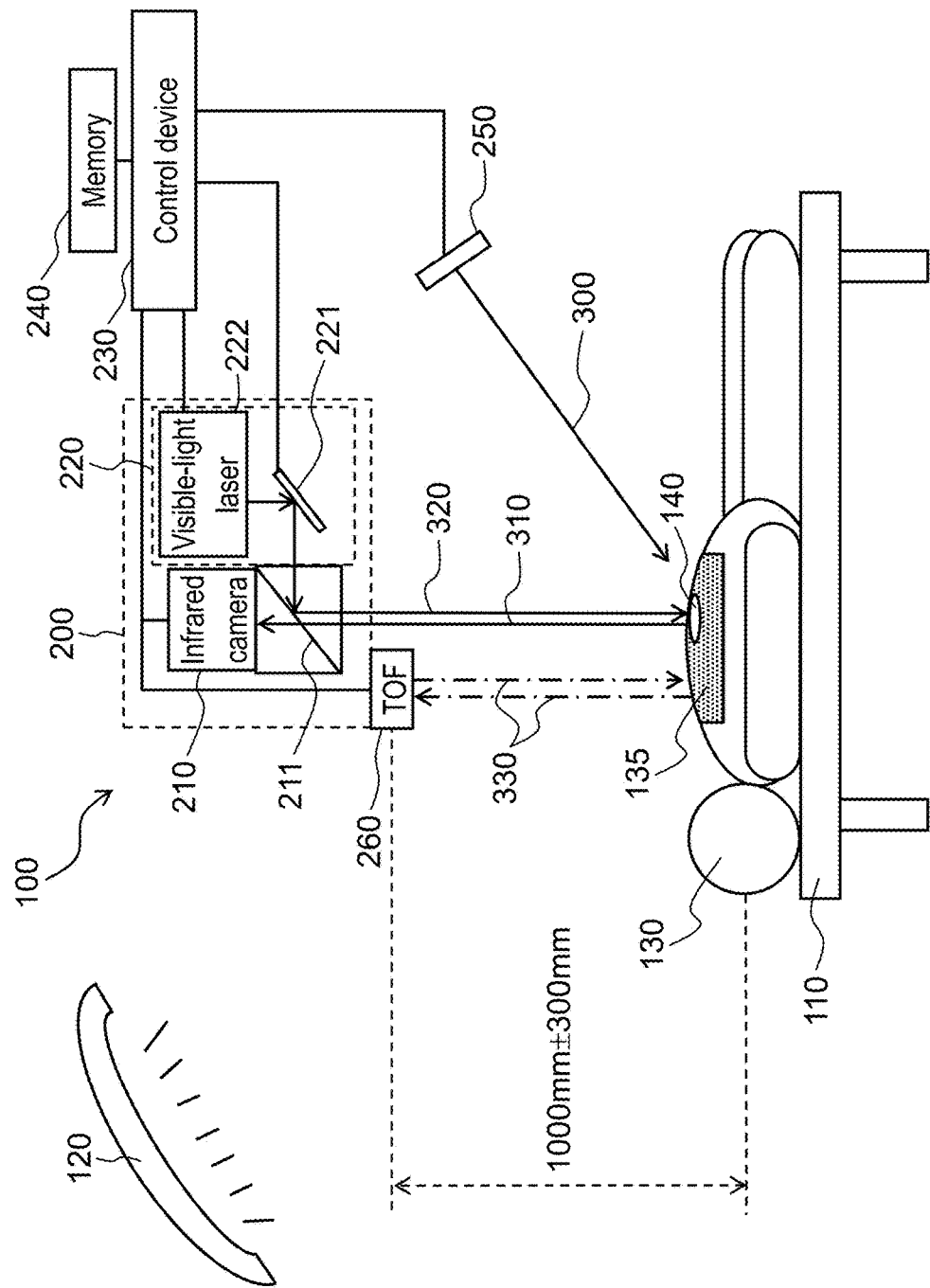
FIG. 1 is a schematic diagram illustrating a configuration of surgery supporting system 100.

The outline of a surgery supporting system according to a first exemplary embodiment will be described with reference to FIG. 1 as one example of the projection system according to the present disclosure. FIG. 1 is a schematic diagram illustrating a configuration of surgery supporting system 100 according to the first exemplary embodiment.

Surgery supporting system 100 is a system that visually supports surgery performed on a patient by a doctor or the like in a surgery room or the like using a projection image with respect to a subject, that is, the patient. When surgery supporting system 100 is used, a light-sensitive substance is administered into blood or the like of patient 130 who undergoes surgery.

The light-sensitive substance emits fluorescence in response to excitation light. The first exemplary embodiment describes the case in which indocyanine green (hereinafter referred to as "ICG") is used as one example of the light-sensitive substance. The ICG is a reagent medically approved and usable for a human body. The ICG emits infrared fluorescence having a wavelength of around 850 nm which is the peak wavelength when irradiated with infrared excitation light having a wavelength of around 800 nm. When administered into blood, the ICG accumulates on affected part 140 where blood or lymph is stagnant. Therefore, the area of affected part 140, which is a specific area, can be specified by detecting an infrared fluorescence area emitting infrared fluorescence.

In this case, since the infrared fluorescence emitted from the area of affected part 140 is non-visible, a doctor or the like cannot directly specify the area of affected part 140 even by visually observing surgical field 135. In view of this, surgery supporting system 100 firstly detects an area of ICG emitting infrared fluorescence to specify the area of affected part 140. Then, surgery supporting system 100 emits visible light to the specified area of affected part 140 in order to enable the specified area of affected part 140 to be visually recognizable by a human. Thus, a projection image that enables the specified area of affected part 140 to be visible is projected, whereby surgery supporting system 100 can support identification of the area of affected part 140 by the doctor or the like who performs surgery.

2. Configuration of Surgery Supporting System

The configuration of surgery supporting system 100 will be described below with reference to FIG. 1. Surgery supporting system 100 is installed and used in a surgery room in a hospital. Surgery supporting system 100 includes imaging irradiation device 200, control device 230, memory 240 serving as a storage unit, and infrared excitation light source 250 serving as a light source unit. Although not illustrated, surgery supporting system 100 also includes a mechanism for changing the position where imaging irradiation device 200 is disposed. This mechanism includes, for example, a drive arm mechanically connected to imaging irradiation device 200 or a caster for a pedestal on which a set of surgery supporting system 100 is placed.

Imaging irradiation device 200 integrally includes imaging means and irradiation means. Imaging irradiation device 200 includes infrared camera 210 serving as an imaging unit, dichroic mirror 211 serving as an optical unit, projector 220, and TOF (Time-of-Flight) sensor 260. Projector 220 includes visible-light laser 222 and MEMS (Micro Electro Mechanical System) mirror 221.

Control device 230 provided in a controller generally controls each component of surgery supporting system 100. Control device 230 is electrically connected to infrared camera 210, visible-light laser 222, MEMS mirror 221, TOF sensor 260, memory 240, and infrared excitation light source 250 and outputs a control signal for controlling each component. Control device 230 includes a CPU or an MPU, for example, and implements its function by executing a predetermined program. Notably, the function of control device 230 may be implemented by an exclusively designed electronic circuit or a reconfigurable electronic circuit (ASIC, FPGA, etc.).

Memory 240 includes a ROM (Read Only Memory) or a RAM (Random Access Memory), for example. Memory 240 is a recording medium accessed by control device 230 as necessary when control device 230 executes various calculations.

Infrared excitation light source 250 emits infrared excitation light 300 with a spectrum including at least a wavelength range component around 800 nm which is the excitation wavelength of the ICG. Infrared excitation light source 250 can switch the on/off of the irradiation of infrared excitation light 300 according to the control signal from control device 230. In the example illustrated in FIG. 1, infrared excitation light source 250 is disposed outside imaging irradiation device 200. However, it is not limited thereto. That is, infrared excitation light source 250 may be disposed inside imaging irradiation device 200, if an irradiation opening for infrared excitation light is appropriately formed.

Notably, since ICG is used in the present exemplary embodiment, infrared excitation light is emitted as light having a predetermined wavelength, and due to this light, affected part 140 emits infrared fluorescence, by which affected part 140 is specified. The specified affected part 140 is projected using visible light. However, it is not limited thereto. For example, visible light may be used as excitation light, and light excited by this excitation light may be visible light. Further, specified affected part 140 may be projected using visible light to make the excited light visually recognizable (to emphasize the excited light). The same is also applied to the case where ultraviolet light is used in place of infrared light or visible light. Light having any wavelength may be used for light to be emitted and light to be excited, and one of them may be visible light, and other may be non-visible light.

Next, the configuration of each component composing imaging irradiation device 200 will be described.

Infrared camera 210 used for an imaging unit is a camera that has spectral sensitivity characteristics with high light reception sensitivity in an infrared region. Surgery supporting system 100 according to the present exemplary embodiment needs to detect infrared fluorescence having a wavelength of around 850 nm from the ICG. For this, infrared camera 210 having spectral sensitivity characteristics with high light reception sensitivity for at least an infrared region with a wavelength around 850 nm is used. It is to be noted that, to prevent light other than the infrared fluorescence from the ICG from being received, a band pass filter that only allows passage of light having a wavelength of about 850 nm may be provided in front of the imaging surface of infrared camera 210. The wavelength spectrum of the infrared fluorescence is one example of a first spectrum. Infrared camera 210 transmits a captured image (infrared image) indicating the capturing result to control device 230.

Visible-light laser 222 is a laser device that emits visible light in projector 220. A laser light source with an arbitrary wavelength may be used for visible-light laser 222, so long as it emits light in a visible light region visually recognizable by a human. Visible-light laser 222 may include a laser light source of one color, or may be configured such that laser light sources of multiple colors may be switchable according to a control signal from control device 230. Visible-light laser 222 emits visible laser light 320 to MEMS mirror 221.

MEMS mirror 221 has a lot of micro-mirror surfaces arranged on a plane, and includes a digital mirror device, for example. Visible laser light 320 emitted from visible-light laser 222 is incident on each of the micro-mirror surfaces of MEMS mirror 221. MEMS mirror 221 reflects visible laser light 320 in the direction according to the tilt angle of each of the micro-mirror surfaces, thereby generating a projection image of visible light.

Here, control device 230 controls the tilt angle of each of the micro-mirror surfaces of MEMS mirror 221 horizontally and vertically. Thus, control device 230 can two-dimensionally scan visible laser light 320 in the vertical direction and in the horizontal direction, thereby being capable of generating a projection image. Visible laser light 320 reflected on the micro-mirror surfaces of MEMS mirror 221 reaches dichroic mirror 211.

Although the present exemplary embodiment illustrates MEMS mirror 221 as one example of the component of projector 220, it is not limited thereto. For example, a galvano mirror may be used. That is, any arbitrary optical element can be used, so long as it enables scanning in the horizontal direction and scanning in the vertical direction.

Dichroic mirror 211 is disposed to face each of infrared camera 210 and MEMS mirror 221. Dichroic mirror 211 is an optical element having a function of transmitting light having a specific wavelength range component (including a wavelength of 850 nm) in incident light and reflecting light having other wavelength range components (including visible-light component). In the present exemplary embodiment, MEMS mirror 221 is disposed in the horizontal direction of dichroic mirror 211, and infrared camera 210 is disposed above dichroic mirror 211 in the vertical direction, as illustrated in FIG. 1. Due to the above optical characteristic, dichroic mirror 211 reflects visible laser light 320 emitted from visible-light laser 222 but transmits infrared fluorescence 310 directed to the imaging surface of infrared camera 210.

Also, as illustrated in FIG. 1, dichroic mirror 211, projector 220, and infrared camera 210 are positioned such that the optical path of visible laser light 320 reflected by dichroic mirror 211 and the optical path of infrared fluorescence 310 incident on the imaging surface of infrared camera 210 coincide with each other. Specifically, between imaging irradiation device 200 and affected part 140, the optical axis of visible laser light 320 and the optical axis of infrared fluorescence 310 are substantially the same. Thus, the precision in emitting visible laser light 320 to the area (affected part 140) emitting infrared fluorescence 310 can be enhanced.

TOF sensor 260 detects distance information indicating a distance from itself to an object by radiating infrared detection light 330 and receiving infrared detection light 330 reflected on the object. The wavelength spectrum of infrared detection light 330 is one example of a second spectrum. TOF sensor 260 uses infrared light with a wavelength of 850 nm to 950 nm as infrared detection light 330. The second spectrum can be at least partly superimposed on the first spectrum. TOF sensor 260 measures the distance from itself to the object on the basis of a lag time from the radiation of infrared detection light 330 till the reception of infrared detection light 330 reflected on the object and light speed. Alternatively, TOF sensor 260 may measure the distance from itself to the object on the basis of the difference between the voltage value of infrared detection light 330 when emitted and the voltage value of infrared detection light 330 when received after being reflected on the object. TOF sensor 260 transmits the distance information concerning the measured distance from itself to the object to control device 230.

Also, as illustrated in FIG. 1, surgical bed 110, shadowless lamp 120, and the like are installed in the surgery room in addition to surgery supporting system 100. Surgical bed 110 is a table on which patient 130 is laid. Shadowless lamp 120 is an illumination tool that illuminates affected part 140 of patient 130 lying on surgical bed 110. Shadowless lamp 120 emits light having high illuminance (30,000 lux to 100,000 lux) for preventing the work area of the doctor from being shadowed.

Surgery supporting system 100 is placed such that imaging irradiation device 200 is located vertically above patient 130 lying on surgical bed 110. In surgery supporting system 100 according to the present exemplary embodiment, an allowable range of a use height is specified on the basis of the focal length determined by the optical system in infrared camera 210 to ensure the precision in specifying the area of affected part 140 by infrared camera 210. In the present exemplary embodiment, the height of 1000 mm±300 mm from the body axis of patient 130 lying on surgical bed 110 to imaging irradiation device 200 (TOF sensor 260) is specified as the allowable range of a use height. The allowable range of height will be described in detail below.

3. Basic Operation of Surgery Supporting System

Next, the activation operation and projection operation, which are the basic operation of surgery supporting system 100, will be described.

3-1. Activation Operation of Surgery Supporting System

Firstly, the activation operation of surgery supporting system 100 will be described. When a power source (not illustrated) is switched to on from off in surgery supporting system 100, control device 230 is activated. Activated control device 230 executes the activation operation of the components composing surgery supporting system 100, such as infrared camera 210, visible-light laser 222, infrared excitation light source 250, and TOF sensor 260.

After the activation operation is executed, visible-light laser 222 starts an amplifying operation of visible laser light 320. Imaging irradiation device 200 is usable at the timing at which the output of visible laser light 320 is stabilized.

3-2. Basic Projection Operation of Surgery Supporting System

Figure 2A:
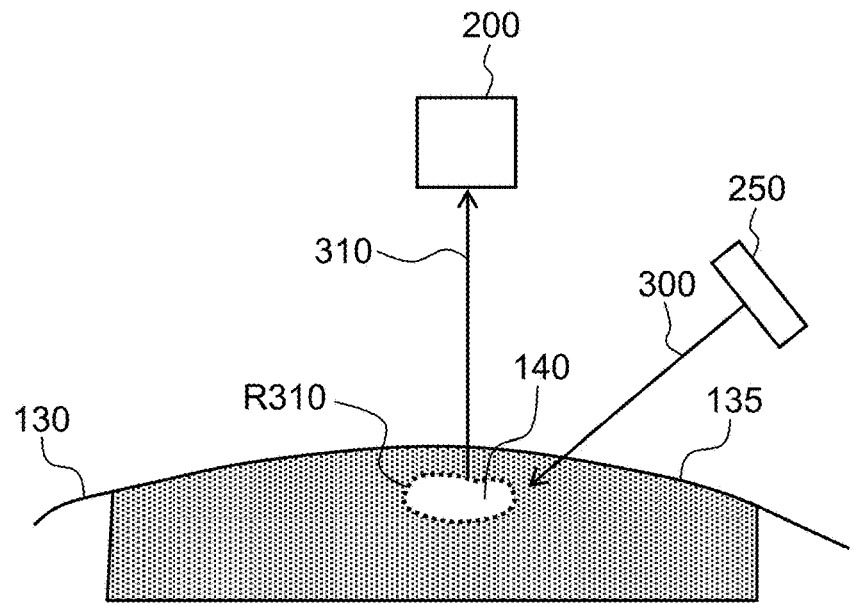
FIG. 2A is a diagram illustrating the state of a surgical field before a projection operation is performed in the surgery supporting system 100.
Figure 2B:
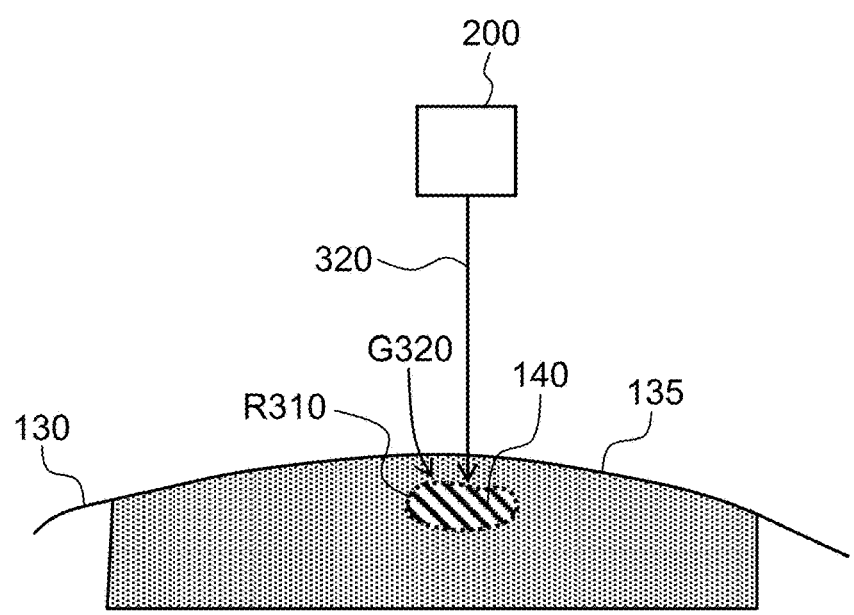
FIG. 2B is a diagram illustrating the state in which the projection operation is performed on the surgical field in FIG. 2A.

Next, the basic projection operation of surgery supporting system 100 will be described with reference to FIGS. 1, 2A, and 2B. FIGS. 2A and 2B are diagrams illustrating the state of surgical field 135 in surgery supporting system 100 in FIG. 1. FIG. 2A is a diagram illustrating the state of surgical field 135 before the projection operation is performed in surgery supporting system 100. FIG. 2B is a diagram illustrating the state in which the projection operation is performed on surgical field 135 in FIG. 2A.

In the state illustrated in FIG. 2A, control device 230 firstly drives infrared excitation light source 250 to emit infrared excitation light 300 to surgical field 135 including affected part 140. Then, infrared excitation light 300 excites the ICG accumulated on affected part 140 in surgical field 135, so that affected part 140 emits infrared fluorescence 310.

Next, infrared camera 210 captures an image of affected part 140 in surgical field 135 under the control of control device 230. At that time, the captured image includes an image of infrared fluorescence area R310 from which infrared fluorescence 310 is emitted. Infrared camera 210 transmits the captured image to control device 230.

Control device 230 detects infrared fluorescence area R310 on the basis of the captured image transmitted from infrared camera 210. Specifically, control device 230 calculates an XY coordinate from a vertex of the captured image to acquire information indicating the coordinate of infrared fluorescence area R310 in the captured image.

Memory 240 stores information indicating the correspondence relation between a coordinate in the captured image from infrared camera 210 and a coordinate in the data for generating a projection image with MEMS mirror 221. Control device 230 controls MEMS mirror 221 such that visible laser light 320 is emitted to the coordinate corresponding to the acquired coordinate on the basis of the information indicating the correspondence relation stored in the storage unit, i.e., memory 240. Notably, projector 220 is controlled to scan and emit visible laser light 320.

When visible laser light 320 is emitted, as illustrated in FIG. 2B, projection image G320 due to visible laser light 320 is projected onto infrared fluorescence area R310 in surgical field 135. In this way, in surgery supporting system 100, infrared fluorescence area R310 is detected on the basis of the captured image by infrared camera 210, whereby the area of affected part 140 emitting invisible infrared fluorescence 310 is specified. Further, the area of affected part 140 which is not directly visually recognizable can be made visible in the surgical field due to the appropriate projection of projection image G320 by projector 220. Notably, projection image G320 is a monochrome uniform image by visible-light laser 222, for example.

The process described above is repeatedly executed in a predetermined cycle (for example, 1/60 second). Thus, a captured image is projected once per 1/60 second, for example, whereby a doctor or the like can visually recognize the position and shape of affected part 140 in real time.

4. Method for Adjusting Projection Shift in Surgery Supporting System

4-1. Outline of Method for Adjusting Projection Shift

As described above, surgery supporting system 100 detects affected part 140 which is not visually recognizable and emits infrared fluorescence 310 from ICG, using infrared camera 210 (see FIG. 2A), and projects a projection image due to visible laser light 320 to make affected part 140 visible using projection image G320 (see FIG. 2B). If projection image G320 is projected as being shifted from infrared fluorescence area R310 of affected part 140 while surgery supporting system 100 is used, the position or the like of affected part 140 may be falsely recognized in surgical field 135. Therefore, before surgery supporting system 100 is used, the relation between the position specified on the basis of the captured image of infrared camera 210 and the projection position of the projection image is confirmed, and if there is a positional shift, surgery supporting system 100 needs to be adjusted.

The confirmation of positional shift and adjustment of positional shift are performed in various situations before surgery supporting system 100 is used. For example, the adjustment of positional shift is performed when the arrangement in imaging irradiation device 200 is determined so as to allow visible-light laser 222 to emit visible laser light 320 to the area specified by infrared camera 210 in a production step. In addition, the adjustment is performed also in the assembling step of imaging irradiation device 200, since a very small error may be generated between the irradiation position of visible-light laser 222 and the imaging position of the infrared camera. Further, disturbance after the assembly and a difference in the angle of view between infrared camera 210 and projector 220 also cause a positional shift. Since ensuring the safety is important in medical application, whether or not there is a positional shift needs to be confirmed every time before the start of surgery using surgery supporting system 100.

According to the present invention, a target to be captured by infrared camera 210 is easily made visible, and a positional shift of a projection image can be easily visually recognized. Due to the method for adjusting a positional shift using an optical adjustment device, the shift between the irradiation position of visible-light laser 222 and the imaging position of infrared camera 210 can easily be adjusted.

The configuration of the optical adjustment device and the method for adjusting a shift using the optical adjustment device will be sequentially described.

Figure 3:
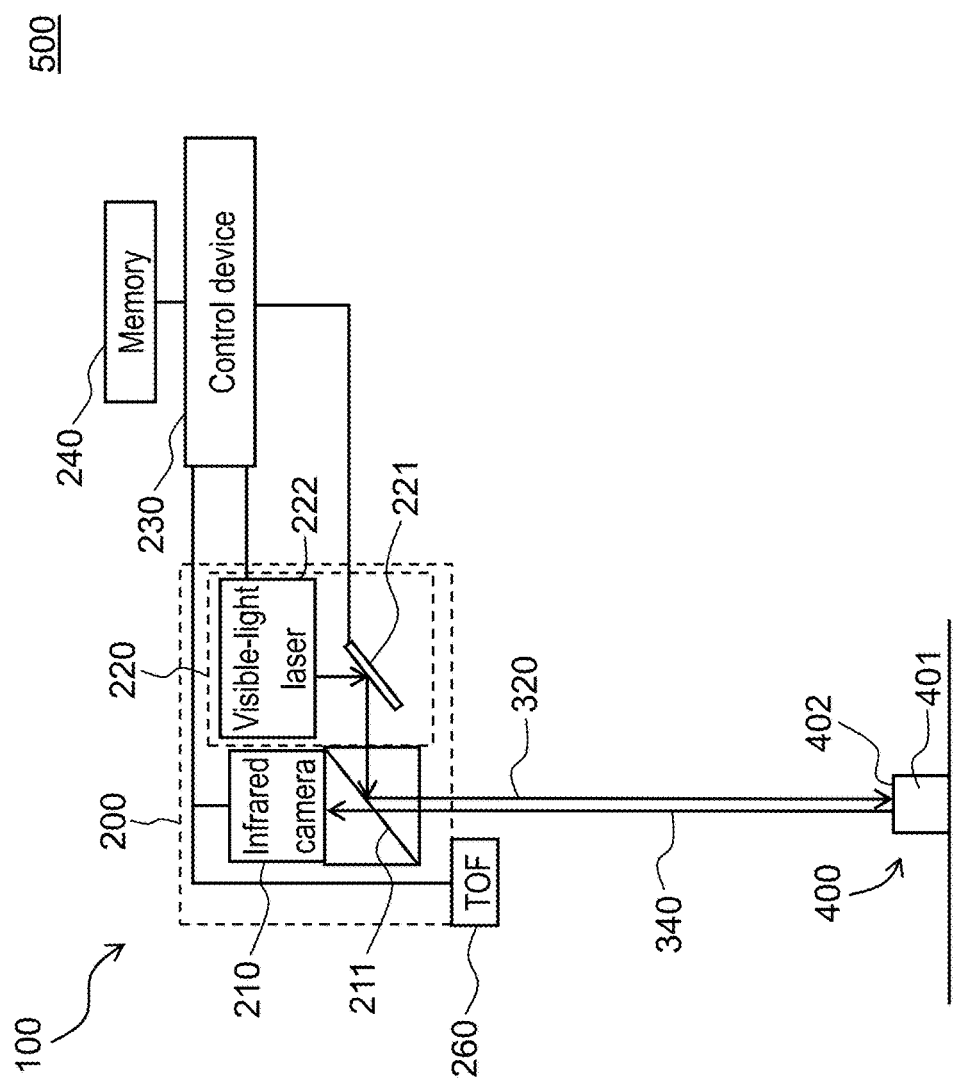
FIG. 3 is a schematic diagram illustrating a configuration of a shift adjustment system 500.
Figure 4A:
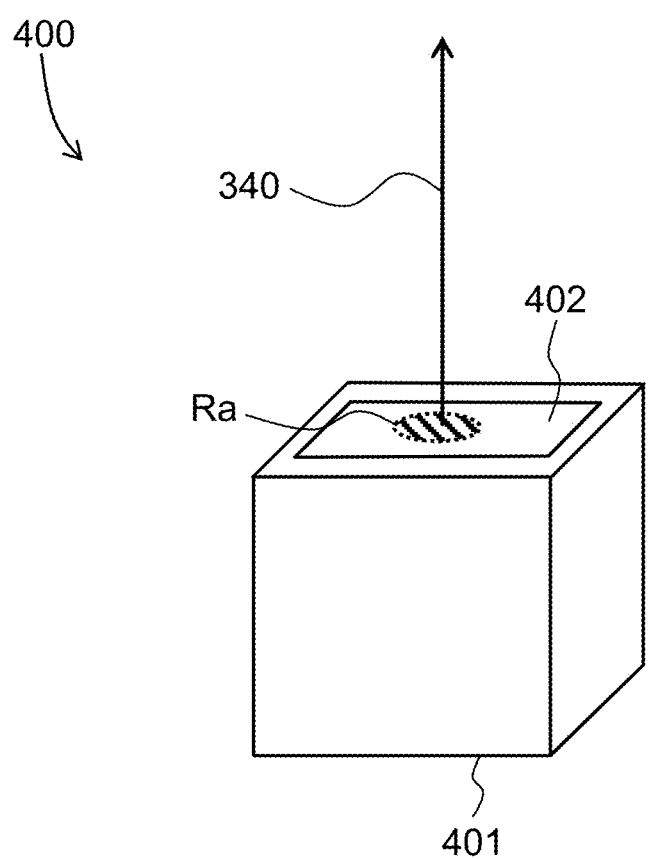
FIG. 4A is a perspective view illustrating an appearance of optical adjustment device 400.
Figure 4B:
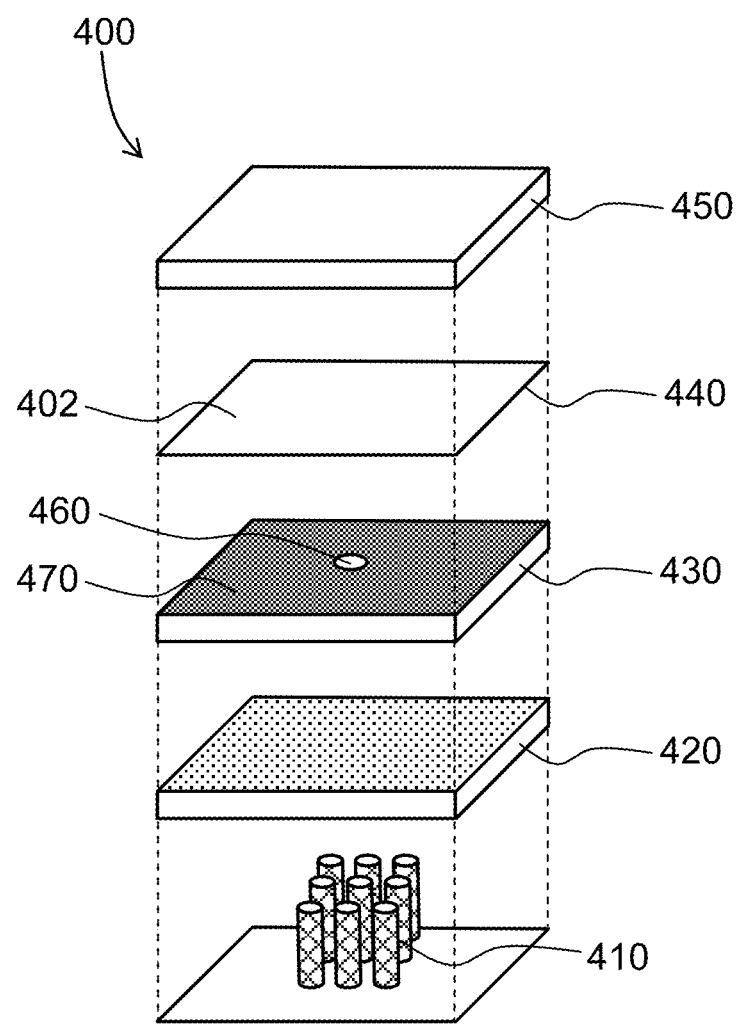
FIG. 4B is an exploded perspective view illustrating the configuration of optical adjustment device 400.

4-2. Configurations of Shift Adjustment System and Optical Adjustment Device The configuration of optical adjustment device will be described with reference to FIGS. 3, 4A, and 4B. FIG. 3 is a schematic diagram illustrating the configuration of shift adjustment system 500 that adjusts a shift between the irradiation position of visible-light laser 222 and the imaging position of infrared camera 210. FIGS. 4A and 4B are views for describing the configuration of optical adjustment device 400. FIG. 4A is a perspective view illustrating an appearance of optical adjustment device 400. FIG. 4B is an exploded perspective view illustrating the configuration of optical adjustment device 400.

Shift adjustment system 500 includes surgery supporting system 100 and optical adjustment device (light source device) 400. Shift adjustment system 500 is one example of a projection system. FIG. 3 illustrates the arrangement state of optical adjustment device 400 with respect to surgery supporting system 100 in shift adjustment system 500. As illustrated in FIG. 3, optical adjustment device 400 has projection surface 402, which is a target of the imaging and projection operations of surgery supporting system 100, on one surface of box-like housing 401, and includes a light source in housing 401. As illustrated in FIG. 4A, projection surface 402 of optical adjustment device 400 is also an emission surface of LED (Light Emitting Diode) light 340 emitted from the inside of housing 401. FIG. 4B illustrates the internal structure of housing 401 of optical adjustment device 400. As illustrated in FIG. 4B, optical adjustment device 400 includes white LED 410, diffusion plate 420, opening mask 430, screen material 440, and protection glass 450. Optical adjustment device 400 has the structure in which white LED 410, diffusion plate 420, opening mask 430, screen material 440, and protection glass 450 are stacked in this order in housing 401.

White LED 410 is a semiconductor light-emitting element that emits white LED light 340. The wavelength spectrum of light emitted from white LED 410 includes a non-visible light region (including an infrared region) as well as a visible light region. In the present disclosure, white LED 410 is used as the light source of optical adjustment device 400. However, it is not limited thereto. In place of white LED 410, a light source having a spectrum including a visible light component and a non-visible light component (including an infrared wavelength component) may be used. For example, both of a light-emitting element that emits only visible light, such as a monochrome LED, and a light-emitting element that emits only infrared light may be disposed in housing 401 to constitute a light source. Alternatively, an arbitrary light source that can coaxially emit visible light and infrared light may be used.

Diffusion plate 420 is made of a resin plate having a rough grounded glass surface, for example. Diffusion plate 420 is disposed to face white LED 410 in housing 401. Diffusion plate 420 reduces brightness unevenness of light emitted from white LED 410 and emits the resultant light from surfaces. Notably, optical adjustment device 400 may not include diffusion plate 420.

Opening mask 430 is a light-shielding member having opening 460 formed on light-shielding surface 470. Opening mask 430 is disposed to face white LED 410 through diffusion plate 420 in housing 401 of optical adjustment device 400. Opening 460 is a hole facing white LED 410 and having a predetermined size, and light emitted from white LED 410 passes through opening 460. Light-shielding surface 470 encloses opening 460 to shield light incident from white LED 410. The size of opening 460 or the location on light-shielding surface 470 of opening mask 430 is determined according to the purpose of measurement. For example, opening 460 with a size of 2 mm or less is formed on opening mask 430 to confirm whether or not a shift is 2 mm or less.

Screen material 440 is a sheet-like member having light-scattering property, and has projection surface 402 on one main surface. Screen material 440 is disposed to face opening mask 430 with its main surface, which is not projection surface 402, facing opening mask 430. At least a visible-light component of light emitted from white LED 410 is scattered on screen material 440. Thus, a viewing angle of reference area Ra, which is an area irradiated with light emitted from white LED 410 and radiating this light, is increased as illustrated in FIG. 4A, and therefore, reference area Ra can be easily visually recognized by a human. Reference area Ra irradiated with light from white LED 410 is formed to have a size according to the setting of opening 460, and serves as a reference for visually recognizing a positional shift in the shift adjustment method described below.

The material of screen material 440 is paper, for example. The color of paper is arbitrary, and a color (for example, complementary color) which facilitates visual recognition according to the color of emitted laser light may be used. Alternatively, cloth may be used for the material of screen material 440 instead of paper. An arbitrary material that scatters at least a part of visible-light component of incident light and has small scattering rate of an infrared wavelength component may be used as the material of screen material 440.

Protection glass 450 is a glass member that protects screen material 440 from having scratches. Notably, optical adjustment device 400 may not include screen material 440 and protection glass 450.

4-3. Shift Adjustment Method Using Optical Adjustment Device

Figure 5A:
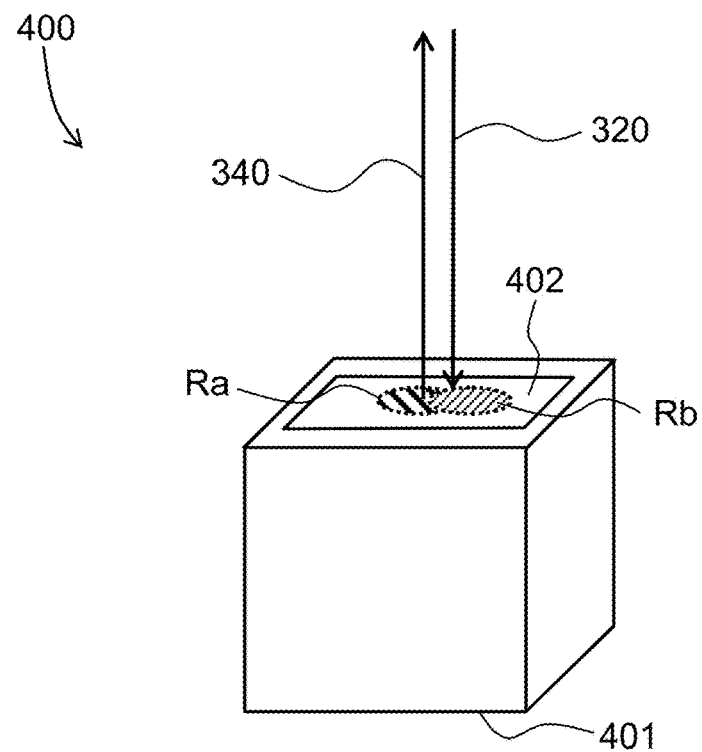
FIG. 5A is a perspective view of optical adjustment device 400 during shift adjustment.
Figure 5B:
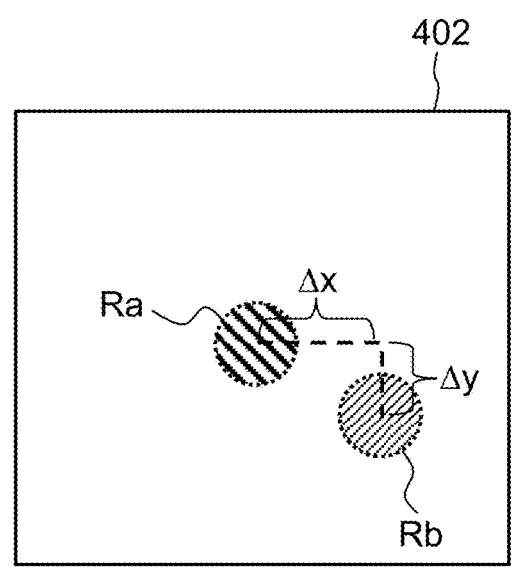
FIG. 5B is a view illustrating one example of a state of projection surface 402 when shift adjustment has not yet been performed.
Figure 5C:
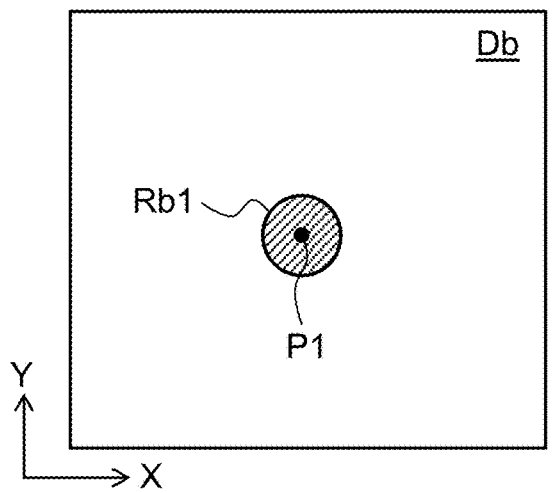
FIG. 5C is a view illustrating an image for projection in the example of FIG. 5B.
Figure 5D:
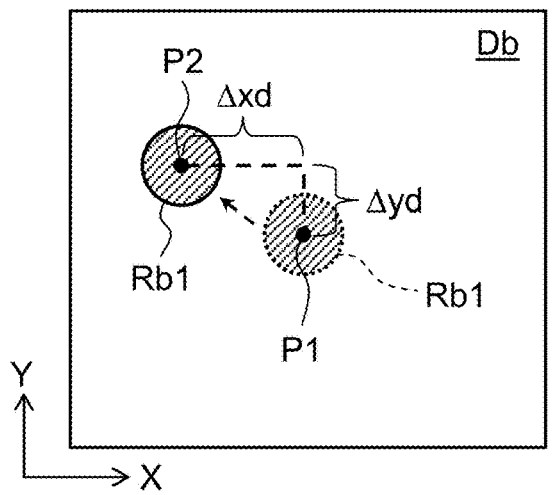
FIG. 5D is a view illustrating an image for projection obtained by performing the shift adjustment on the image in FIG. 5C.
Figure 5E:
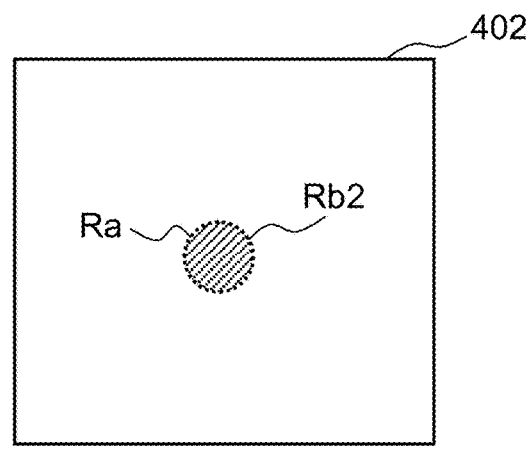
FIG. 5E is a view illustrating one example of a state of projection surface 402 after the shift adjustment.

Next, the shift adjustment method using optical adjustment device 400 will be described with reference to FIGS. 3 and 5A to 5E. FIGS. 5A to 5E are views for describing shift adjustment using optical adjustment device 400. FIG. 5A is a perspective view of optical adjustment device 400 during shift adjustment. FIG. 5B is a view illustrating one example of a state of projection surface 402 when the shift adjustment has not yet been performed. FIG. 5C is a view illustrating an image for projection in the example of FIG. 5B. FIG. 5D is a view illustrating an image for projection obtained by performing the shift adjustment on the image in FIG. 5C. FIG. 5E is a view illustrating one example of a state of projection surface 402 after the shift adjustment.

The present adjustment method is performed by, for example, an operator for adjustment of a manufacturer as an adjustment operation in a production step of imaging irradiation device 200 or surgery supporting system 100. In this case, shipped items of imaging irradiation device 200 or surgery supporting system 100 have already been adjusted. The present adjustment method can also be performed as a precautionary confirmation operation just before actual surgery, even if adjustment has already been performed in the production step.

When performing the present adjustment method, an operator for adjustment places optical adjustment device 400 at the position just below imaging irradiation device 200 and facing the imaging surface of infrared camera 210 and irradiation opening of visible laser light 320 as illustrated in FIG. 3. At that time, if the height allowable range, which is an allowable range of the distance (height) between imaging irradiation device 200 and surgical bed 110, is set as 1000 mm±300 mm, optical adjustment device 400 is placed at the position 1000 mm from the lower surface of imaging irradiation device 200.

After placing optical adjustment device 400, the operator for adjustment allows white LED 410 to emit LED light 340.

LED light 340 is incident on screen material 440 through opening mask 430, and emitted from reference area Ra on projection surface 402. The visible-light component of LED light 340 generates scattering light on screen material 440. The scattering light of the visible-light component of LED light 340 forms an image (hereinafter referred to as "reference area image" Ra) indicating reference area Ra on projection surface 402 (see FIG. 4A).

LED light 340 emitted from white LED 410 includes a wavelength range component of an infrared region. The wavelength range component for the infrared region in LED light 340 passes through dichroic mirror 211 of surgery supporting system 100.

Surgery supporting system 100 performs the projection operation described above for projection surface 402 of optical adjustment device 400 as the imaging and projection target. In surgery supporting system 100, infrared camera 210 receives light passing through dichroic mirror 211 and captures an image of projection surface 402. Therefore, infrared camera 210 captures an image of reference area Ra that emits light including the wavelength range component of the infrared region. Infrared camera 210 transmits the captured image to control device (adjustment unit) 230.

Control device 230 calculates, for example, XY coordinate from one vertex of the captured image to acquire information indicating the coordinate of reference area image Ra emitting light with the wavelength range of the infrared region, on the basis of the captured image transmitted from infrared camera 210. Control device 230 manages the coordinate on the captured image transmitted from infrared camera 210 and the scanning coordinate to which visible laser light 320 is to be emitted in one-to-one correspondence on image data, for example. Control device 230 controls MEMS mirror 221 such that visible laser light is emitted to the scanning coordinate corresponding to the acquired coordinate.

Projector 220 emits visible laser light 320 to optical adjustment device 400 according to infrared emission from optical adjustment device 400, thereby projecting projection image Rb on projection surface 402 as illustrated in FIG. 5A. As a result, reference area image Ra that is the imaging target of imaging irradiation device 200 and projection image Rb by imaging irradiation device 200 are projected on projection surface 402 of optical adjustment device 400 by visible light, and the operator for adjustment can visually recognize both images simultaneously.

At that time, reference area image Ra by LED light 340 and projection image Rb by visible laser light 320 have to coincide with each other. However, a positional shift may actually occur between both images due to an assembling error or the like. In such a case, positional shifts Δx and Δy between the position of reference area image Ra and the position of projection image Rb can be visually recognized by means of optical adjustment device 400 as illustrated in FIG. 5B.

The adjustment operation for positional shifts Δx and Δy illustrated in FIG. 5B will be described below.

Firstly, control device 230 stores, in memory 240, information indicating the irradiation position (that is, the scanning position of MEMS mirror 221) of visible laser light 320 when the shift adjustment has not yet been performed. In this case, control device 230 generates an image signal indicating image Db in which projection image Rb1 is formed based on the capturing result of reference area image Ra as illustrated in FIG. 5C. Projection image Rb by visible laser light 320 is projected on projection surface 402 on the basis of this image signal at the position shifted from reference area image Ra as illustrated in FIG. 5B. Control device 230 stores, in memory 240, unadjusted position P1 of projection image Rb1 on image Db while the shift adjustment has not yet been performed. Position (scanning position) P1 is referred to as an "unadjusted position" below.

The operator for adjustment compares reference area image Ra with projection image Rb projected on projection surface 402 while observing both images, and inputs a shift amount to control device 230 using an operation unit (not illustrated) or the like so as to align both images. Specifically, the operator for adjustment inputs, to control device 230, information concerning an amount of movement for shifting the projection image on an X axis or a Y axis.

Control device 230 controls projector 220 such that the irradiation position (scanning position by MEMS mirror 221) of visible laser light 320 is changed on the basis of the input information. For example, on the basis of the input information indicating the amount of movement, control device 230 shifts the irradiation position on image Db from unadjusted position P1 by amounts of movement Δxd and Δyd indicated by the input information as illustrated in FIG. 5D. Amounts of movement Δxd and Δyd on the image are values corresponding to actual positional shift amounts Δx and Δy on projection surface 402. Due to this adjustment, projection image Rb2 is projected on the position on projection surface 402 corresponding to irradiation position P2 after the adjustment, and aligned with reference area image Ra as illustrated in FIG. 5E.

The operation described above is repeated until the operator for adjustment determines that reference area image Ra and projection image Rb2 projected on projection surface 402 are aligned with each other.

Upon the completion of the adjustment operation, control device 230 stores the last irradiation position P2 (that is, the scanning position of MEMS mirror 221) on image Db in memory 240. Irradiation position (scanning position) P2 is referred to as an "adjusted position" below.

Control device 230 calculates a shift correction amount on the basis of unadjusted position P1 and adjusted position P2 stored in memory 240. Specifically, control device 230 calculates the difference between unadjusted position P1 and adjusted position P2 as a shift correction amount. In the example illustrated in FIGS. 5B to 5E, amounts of movement Δxd and Δyd are stored in memory 240 as the shift correction amount.

After performing the shift adjustment described above, control device 230 corrects the irradiation position of visible laser light 320 on the basis of the shift correction amount stored in memory 240, and projects a projection image. Thus, a projection image can precisely be projected on a projection target.

4-4. Application Example of Optical Adjustment Device 400

Whether or not a positional shift amount falls within an allowable error can be confirmed from a reference area image and a projection image projected on optical adjustment device 400. The confirmation method of an allowable error will be described below with reference to FIG. 6. FIG. 6 illustrates one example of a state of projection surface 402 when optical adjustment device 400 is used while being disposed as illustrated in FIG. 3.

Diameter La of circular reference area image Ra illustrated in FIG. 6 is set to be equal to a predetermined allowable error according to the specification of surgery supporting system 100. Diameter La is set according to the size of opening 460 of opening mask 430 (see FIGS. 4A and 4B). For example, when the specification of surgery supporting system 100 requires projection precision of an allowable error of 2 mm, diameter La is set to be 2 mm. In one example illustrated in FIG. 6, it is supposed that there is no error in projection magnification of projection image Rb.

In the case where reference area image Ra and projection image Rb are partly overlapped with each other as illustrated in FIG. 6, positional shift ΔL between reference area image Ra and projection image Rb becomes equal to or less than diameter La. Therefore, the projection precision of surgery supporting system 100 falls within the allowable error range. On the other hand, when there is no overlapped portion between reference area image Ra and projection image Rb, positional shift ΔL is larger than diameter La, so that the projection precision can be determined to be outside the allowable error range. Accordingly, a user of optical adjustment device 400 can easily confirm whether or not the positional shift falls within the allowable error range by visually recognizing whether or not reference area image Ra and projection image Rb are at least partly overlapped with each other. If the positional shift is confirmed to fall within the allowable error range, the operation of control device 230 for the above-mentioned shift adjustment may not be performed.

Further, in the above description, the shape of reference area image Ra is circular. However, the shape of reference area image Ra is not particularly limited, and reference area image Ra may have an elliptic shape, a polygonal shape such as a triangular shape or a rectangular shape, or other shape. In addition, a plurality of reference areas may be formed on one projection surface 402. As one example, a shift adjustment method in the case where the reference area image is rectangle will be described with reference to FIGS. 7A to 7C.

Figure 7A:
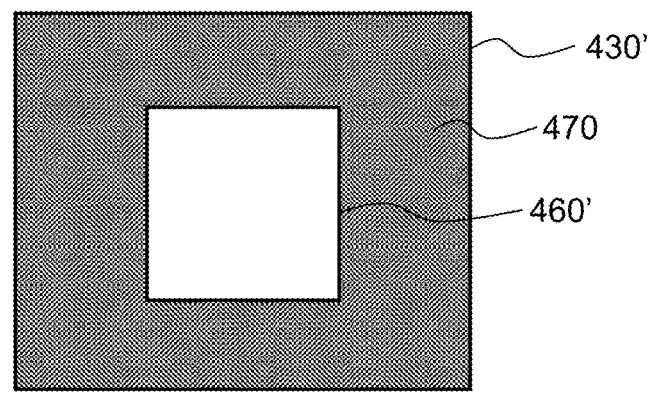
FIG. 7A is a plan view of opening mask 430' in an application example.
Figure 7B:
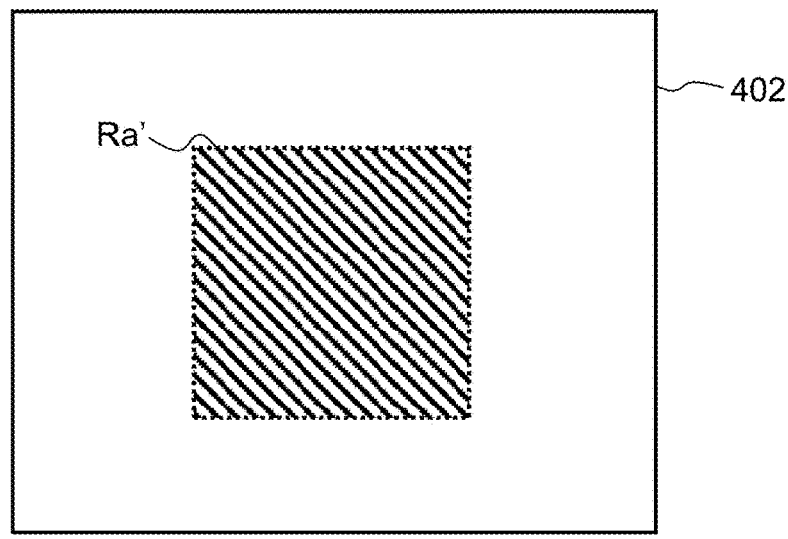
FIG. 7B is a view illustrating a state in which an image is projected on a projection surface using opening mask 430' in FIG. 7A.
Figure 7C:
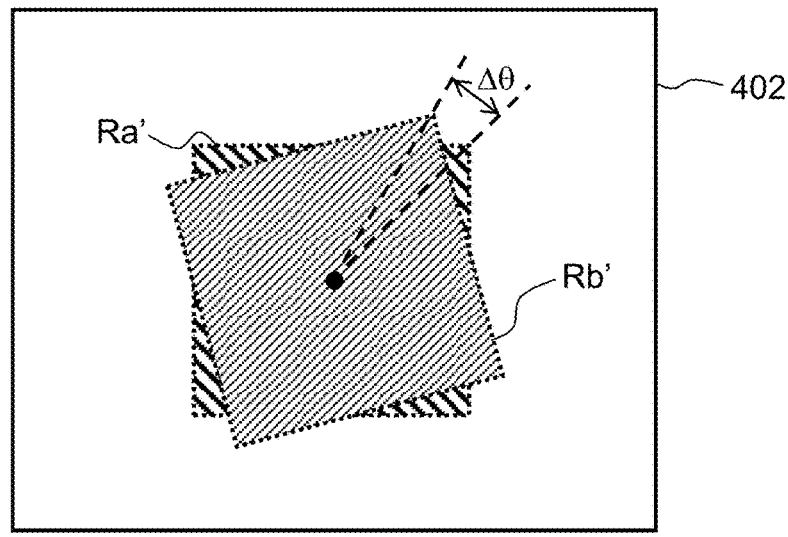
FIG. 7C is a view illustrating the state in which the projection operation of surgery supporting system 100 is performed on the projection surface illustrated in FIG. 7B.

FIG. 7A is a plan view of opening mask 430'. FIG. 7B illustrates the state in which an emission image by white LED 410 is projected on projection surface 402 using opening mask 430'. FIG. 7C illustrates the state in which the projection operation of surgery supporting system 100 disposed as illustrated in FIG. 3 is performed on projection surface 402 illustrated in FIG. 7B.

As illustrated in FIG. 7A, with the use of opening mask 430' having rectangular opening 460', rectangular reference area image Ra' is projected on projection surface 402 as illustrated in FIG. 7B. In this case, whether or not the orientation of reference area image Ra' and the orientation of projection image Rb' are different from each other can be visually confirmed. For example, angular shift $\Delta\theta$ can be visually recognized through comparison between one vertex of reference area image Ra' and one vertex of projection image Rb' as illustrated in FIG. 7C. Therefore, the operator for adjustment can perform adjustment while visually recognizing angular shift $\Delta\theta$, as in the adjustment for positional shifts $\Delta x$ and $\Delta y$.

4-5. Effects, Etc.

As described above, in the present exemplary embodiment, shift adjustment system 500 includes optical adjustment device 400, infrared camera 210, and projector 220. Optical adjustment device 400 has projection surface 402 including reference area Ra, and emits LED light 340 including non-visible light and visible light from reference area Ra. Infrared camera 210 receives non-visible light and captures an image of projection surface 402. Projector 220 projects projection image Rb of visible light on projection surface 402 on the basis of the captured image captured by infrared camera 210.

Thus, LED light including visible light is emitted from reference area Ra included in projection surface 402 of optical adjustment device 400, and projection image Rb of visible light based on the captured image of reference area Ra is projected on projection surface 402. Accordingly, the shift between reference area Ra, which is a subject, on projection surface 402 and its projection image Rb is made visible. Consequently, the projection system, which captures an image of the subject and projects the projection image, can easily adjust the shift between the subject and the projection image.

Further, the shift adjustment method is an adjustment method for adjusting projection image G320 which is to be projected on affected part 140 in surgery supporting system 100. Surgery supporting system 100 includes infrared camera 210 that receives infrared fluorescence 310 and captures an image of affected part 140, and projector 220 that generates projection image G320 of visible light on the basis of the captured image of affected part 140 and projects projection image G320 on affected part 140. The shift adjustment method includes a step of emitting LED light 340 including a spectrum having a visible-light component and infrared wavelength component (including a wavelength of 850 nm) to reference area Ra on projection surface 402 that is the target for imaging and projection operations of surgery supporting system 100. The shift adjustment method includes a step of capturing reference area Ra on projection surface 402 by infrared camera 210. The shift adjustment method includes a step of projecting projection image Rb by projector 220 based on captured reference area Ra on projection surface 402 onto projection surface 402. The shift adjustment method includes a step of comparing reference area Ra with projection image Rb on projection surface 402. The shift adjustment method includes a step of adjusting the position of projection image Rb on the basis of the comparison result.

Further, in the present exemplary embodiment, optical adjustment device 400 is an adjustment device for adjusting projection image G320 which is to be projected on affected part 140 in surgery supporting system 100. Optical adjustment device 400 includes white LED 410 and projection surface 402. White LED 410 emits LED light 340 having a spectrum including a visible-light component and an infrared wavelength component (including a wavelength of 850 nm). Projection surface 402 includes predetermined reference area Ra irradiated with (white) LED light 340 emitted from white LED 410, and becomes a target for imaging and projection operations of surgery supporting system 100.

Thus, while visible laser light 320 is emitted to the area from which infrared fluorescence 310 that is fluorescence of ICG is detected during actual surgery, infrared light included in white LED 410 of optical adjustment device 400 is regarded as infrared fluorescence of ICG during the adjustment operation. With this, the shift between the irradiation position of visible-light laser 222 and the imaging position of infrared camera 210 can be made visible on projection surface 402, and thus, the shift can easily be adjusted. Consequently, visible laser light 320 can accurately be emitted to the area of affected part 140 detected and specified by infrared camera 210.

Notably, while projection surface 402 is a main surface of screen material 440 in the above description, it is not limited thereto. For example, in an optical adjustment device not having screen material 440, light-shielding surface 470 of opening mask 430 may be used as a projection surface. In this case as well, a reference area to which LED light 340 is emitted is formed by opening 460.

In addition, while reference area Ra is formed by opening 460 in the above description, it is not limited thereto. A reference area may be formed by guiding LED light 340 to be incident on projection surface 402 using a reflection mirror or a lens.

Further, in the above description, a projection image is adjusted with a signal process based on a shift correction amount. However, the shift adjustment method according to the present exemplary embodiment is not limited thereto. For example, an operator for adjustment may adjust a physical arrangement of infrared camera 210, visible-light laser 222, or the like while visually observing projection surface 402 of optical adjustment device 400.

In addition, while an operator for adjustment aligns reference area Ra and projection image Rb with each other by operating an operation unit, it is not limited thereto. Control device 230 may compare reference area Ra with projection image Rb on projection surface 402, and adjust the position of the projection image on the basis of the comparison result. The positions of reference area Ra and visible-light area Rb may be specified by capturing projection surface 402 by a visible light camera, and control device 230 may perform position alignment. For example, a number of dots on a captured image by the visible-light camera may be counted, and the counted number may be converted into a correction amount. Control device 230 may execute such a process by using a predetermined program.

While the case in which $\Delta xd$ and $\Delta yd$ are stored in memory 240 as a shift correction amount has been described above, the configuration is not limited thereto. In the case where rotation angle $\theta$ of projection image Rb with respect to reference area Ra and projection magnification Z are changed during alignment between reference area Ra and projection image Rb, correction amount Δθd of rotation angle θ and correction amount ΔZd of projection magnification Z may be stored in memory 240. Notably, projection magnification Z and its correction amount ΔZd may be set according to a zoom value with an optical system for projecting a projection image, such as a zoom lens, or may be set according to a digital value in a signal process for a projection image.

For example, correction amount Δθd can be extracted on the basis of angular shift Δθ illustrated in FIG. 7C. Further, correction amount ΔZd can be extracted by comparison in distance between two vertexes between reference area Ra' and projection image Rb' illustrated in FIG. 7C. In addition, a visible-light camera may capture an image of optical adjustment device 400 in various different arrangement, and reference area image Ra and projection image Rb may be compared in each case to extract and correct distortion of the projection image.

Further, while a shift is adjusted by using one optical adjustment device 400 in the above description, a plurality of optical adjustment devices 400 may be used for shift adjustment. With this, a shift can be adjusted without changing the location of optical adjustment device 400, whereby the adjustment time can be shortened and precision in adjustment can be enhanced.

Further, while the shift adjustment method for the case where projector 220 includes visible-light laser 222 and scans and emits laser has been described above, the projection method of a projection image is not limited thereto. The shift adjustment method using optical adjustment device 400 can also be applied for the case of projecting a projection image with other method.

5. Scanning Operation by Laser Scanning Projection

5-1. Outline of Scanning Operation

In surgery using surgery supporting system 100, lighting devices with high illuminance (30,000 lux to 100,000 lux) such as illumination from shadowless lamp 120 and illumination attached to the head of a doctor may simultaneously be used in some cases. A light source used for an ordinary imaging irradiation device 200 has low illuminance such as about hundreds of lux, so that a projection image is inconspicuous and is not visually recognizable under an environment of high illuminance.

The present invention has devised the feature of employing a laser scanning projection using projector 220 which includes visible-light laser 222 and MEMS mirror 221 in surgery supporting system 100. Specifically, surgery supporting system 100 scans only the inside or boundary of an area of affected part 140, which is detected and specified by infrared camera 210, with visible laser light 320 by MEMS mirror 221, while enabling supply of high-illumination light from visible-light laser 222. Thus, visual recognition of a projection image can be facilitated even under an environment of high illuminance, while in consideration of safety.

5-2. Detail of Scanning Operation

Figure 8A:
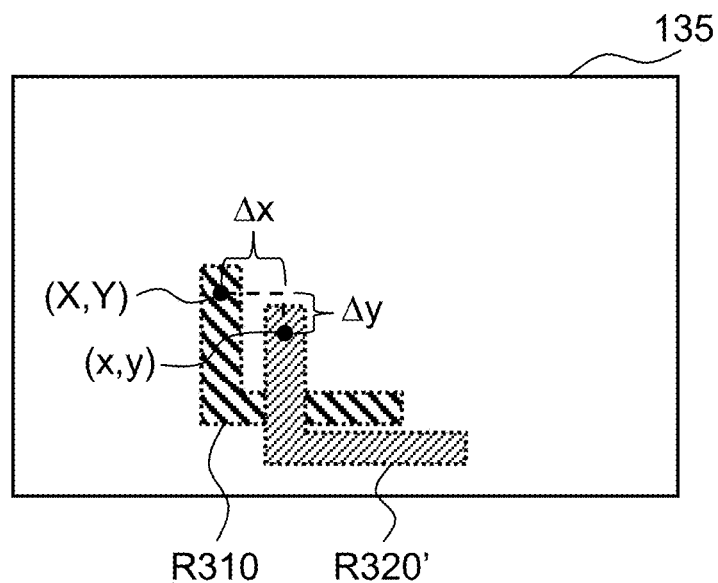
FIG. 8A is a diagram for describing infrared fluorescence 310 and visible laser light 320 before the shift adjustment.
Figure 8B:
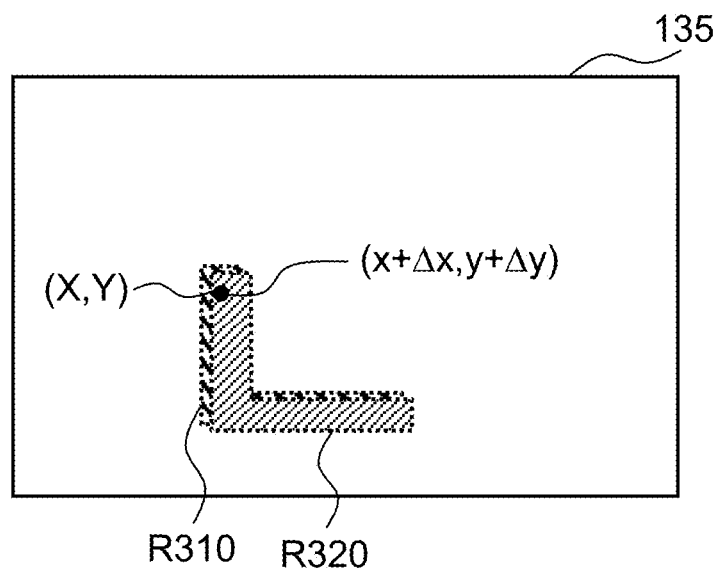
FIG. 8B is a diagram for describing infrared fluorescence 310 and visible laser light 320 after the shift adjustment.

The scanning operation with visible-light laser 222 and MEMS mirror 221 will be described below with reference to FIGS. 1, 8A, 8B, and 9. FIGS. 8A and 8B are diagrams for describing infrared fluorescence 310 and visible laser light 320 before and after the shift adjustment. FIG. 9 is a diagram for describing scanning patterns with visible-light laser 222 and MEMS mirror 221.

As illustrated in FIG. 1, surgical bed 110 on which patient 130 is laid is placed at the position just below imaging irradiation device 200 and facing the imaging surface of infrared camera 210 and irradiation opening of visible laser light 320. In this case, if the allowable range based on the focal length of infrared camera 210 is set as 1000 mm±300 mm, for example, the use height of imaging irradiation device 200 or the use height of surgical bed 110 is adjusted such that the body axis of patient 130 is located at the position 1000 mm from the lower surface of imaging irradiation device 200.

It is supposed that ICG has already been administered into blood of patient 130, and the ICG has accumulated on affected part 140. Patient 130 lies on surgical bed 110 in the state in which a body part having affected part 140 which is to be cut with a scalpel faces upward, and with this state, the operation of surgery supporting system 100 is started.

Firstly, control device 230 causes infrared excitation light source 250 to emit infrared excitation light 300 having a wavelength around the excitation wavelength of 800 nm of the ICG to surgical field 135 near affected part 140 of patient 130. The ICG accumulated on affected part 140 induces an excitation reaction by infrared excitation light 300, thereby emitting infrared fluorescence 310 around a peak wavelength 850 nm. A part of infrared fluorescence 310 emitted from the ICG accumulated on affected part 140 passes through dichroic mirror 211. Infrared camera 210 receives infrared fluorescence 310 passing through dichroic mirror 211 and captures an image of surgical field 135. With this, the image captured by infrared camera 210 includes infrared fluorescence area R310 emitting infrared fluorescence 310. Infrared camera 210 transmits the captured image to control device 230.

Control device 230 specifies the coordinate (for example, XY coordinate from one vertex of the captured image) of the area emitting infrared fluorescence 310 on the basis of the captured image transmitted from infrared camera 210. At that time, control device 230 reads shift correction amounts Δx and Δy stored in memory 240. Control device 230 also calculates a corrected coordinate obtained by correcting the specified coordinate based on the captured image transmitted from infrared camera 210 by the shift correction amounts read from memory 240. Control device 230 controls MEMS mirror 221 such that visible laser light 320 is emitted with a laser scanning pattern which is previously set to a scanning coordinate corresponding to the corrected coordinate of the coordinate in the captured image transmitted from infrared camera 210. The detail of the laser scanning pattern will be described below.

FIG. 8A illustrates infrared fluorescence area R310 of infrared fluorescence 310 from ICG and projection area R320' by visible laser light 320 in the case where the correction based on the shift correction amounts is not performed. When the corrected coordinate corrected by the shift correction amounts is not used, visible laser light 320 is emitted to the position shifted from infrared fluorescence area R310 of ICG by Δx and Δy.

On the other hand, FIG. 8B illustrates infrared fluorescence area R310 of infrared fluorescence 310 from ICG and projection area R320 by visible laser light 320 in the case where the correction based on the shift correction amounts is performed. When the corrected coordinate corrected by the shift correction amounts is used, visible laser light 320 is accurately emitted to infrared fluorescence area R310 of ICG.

As described above, use of the corrected coordinate enables accurate emission of visible laser light 320 to the area of affected part 140 emitting infrared fluorescence 310.

Subsequently, the laser scanning pattern with visible-light laser 222 and MEMS mirror 221 will be described. FIG. 9 illustrates raster scanning and vector scanning that are selectable as the laser scanning pattern in surgery supporting system 100.

Raster scanning is a scanning pattern in which reciprocating emission operation of visible laser light 320 is performed on only the inside of affected part 140 emitting infrared fluorescence 310 so as to fill a face. During the raster scanning illustrated in FIG. 9, the scale of illuminance is set to 1. Upon oscillation in 25 lumens, the illuminance on the irradiated surface is about 2500 lux in the case where the irradiation area is the maximum (100 mm×100 mm), and is about 250,000 lux in the case of the minimum irradiation area (10 mm×10 mm).

Vector scanning is a scanning pattern in which visible laser light 320 is emitted to only the boundary of affected part 140 emitting infrared fluorescence 310 so as to draw a line. During the vector scanning illustrated in FIG. 9, the scale of illuminance is set to 20. Upon oscillation in 25 lumens, the illuminance on the irradiated surface is about 50,000 lux in the case where the irradiation area is the maximum (100 mm×100 mm), and is about five million lux in the case of the minimum irradiation area (10 mm×10 mm).

A doctor can select which one of the visible-light laser irradiation with the raster scanning and the visible-light laser irradiation with the vector scanning is used by operating an operation unit (not illustrated) according to a surgery matter or the like.

Although FIG. 9 illustrates the raster scanning and the vector scanning as the scanning patterns, it is not limited thereto. For example, as a derived pattern of the raster scanning, a pattern may be used in which only the inside of the area of affected part 140 emitting infrared fluorescence 310 is scanned while thinned scanning is performed as necessary. Alternatively, as a derived pattern of the raster scanning or the vector scanning, a pattern in which the same site is continuously scanned more than once, and then, the irradiation position is shifted to the other site may be used.

Control device 230 causes projector 220 to emit visible laser light 320 to the area of affected part 140 emitting infrared fluorescence 310 on the basis of the set scanning pattern so as to project a projection image. In this case, control device 230 controls MEMS mirror 221 such that visible-light laser is emitted on the basis of the set scanning pattern. Control device 230 continues the scanning operation even after a round of scan to the inside or the boundary of the area of affected part 140 emitting infrared fluorescence 310 is completed.

5-3. Effects, Etc.

As described above, in the present exemplary embodiment, surgery supporting system 100 includes infrared camera 210, projector 220, and control device 230. Infrared camera 210 captures affected part 140. Projector 220 generates projection image G320 of visible light on the basis of the captured image captured by infrared camera 210, and projects projection image G320 onto affected part 140. Control device 230 controls the operations of infrared camera 210 and projector 220. Projector 220 includes visible-light laser 222 that emits visible laser light 320. Control device 230 controls projector 220 such that projection area R320 on which projection image G320 is projected is scanned with visible laser light 320 with a predetermined scanning pattern.

Since surgery supporting system 100 uses a laser light source having high illuminance as an irradiation light source, visibility can be enhanced even under the environment with high illuminance by other lighting devices such as shadowless lamp 120. Further, since only an inside or a boundary of a specific area is scanned with a predetermined scanning pattern, illuminance can be obtained in comparison with irradiation to a wide area, whereby visibility can be enhanced. Further, surgery supporting system 100 is not configured to continuously emit high-illuminance visible laser light 320 to the same position, but to scan an irradiation position. Thus, surgery supporting system 100 that facilitates visual recognition even under an environment of high illuminance, while taking into consideration of safety, can be provided.

The scanning pattern may be raster scanning in which visible laser light 320 scans the inside of projection area R320. Alternatively, the scanning pattern may be vector scanning in which visible laser light 320 scans along the boundary of projection area R320.

Projector 220 may further include MEMS mirror 221 having multiple micro-mirror surfaces that reflect visible laser light 320. Control device 230 may control projector 220 such that visible laser light 320 is scanned by changing the tilt angle of each of micro-mirror surfaces on MEMS mirror 221. Thus, the processing amount during the scan of visible laser light 320 can be reduced.

6. Projection Operation of Cutting Aid Line According to Detection of Affected Part 6-1. Outline of Projection Operation of Cutting Aid Line A doctor has to determine a cutting position which is to be cut with a scalpel before the start of surgery for affected part 140. Therefore, the doctor performs work for confirming the relation between affected part 140 and the cutting position which is to be cut with a scalpel on an image analysis device or the like. In this case, the doctor plans the cutting position so as to put the scalpel into affected part 140 with a margin of a certain distance. Then, the doctor prepares for surgery with the planned cutting position in mind.

However, it is not easy to precisely reproduce the cutting position planned before the start of the surgery, and this imposes a strain on the doctor. Further, the work described above takes much time for preparation before the start of the surgery.

In view of this, the inventor of the present disclosure has conceived of projecting cutting aid line 321, as associated information, for aiding determination of the cutting position which is to be cut with a scalpel as well as projecting projection image G320 of visible light displaying the area of affected part 140 on which ICG is accumulated. According to this, the reproduction of the cutting position planned before the start of the surgery can be assisted, whereby the burden of the doctor can be reduced. Further, the time for preparation before the start of the surgery can be shortened.

6-2. Detail of Projection Operation of Cutting Aid Line

Figure 10:
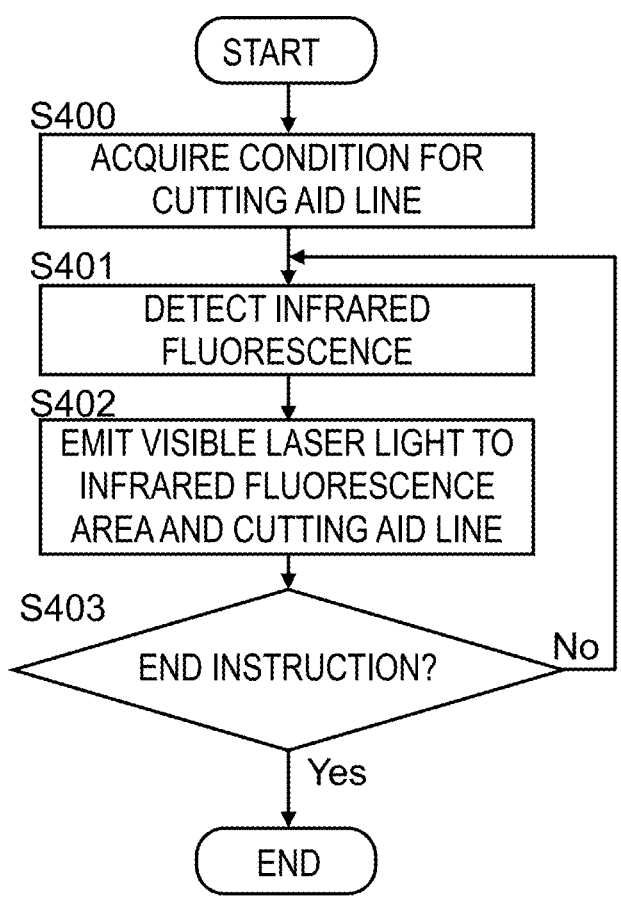
FIG. 10 is a flowchart illustrating the projection operation of a cutting aid line according to the detection of an affected part.
Figure 11A:
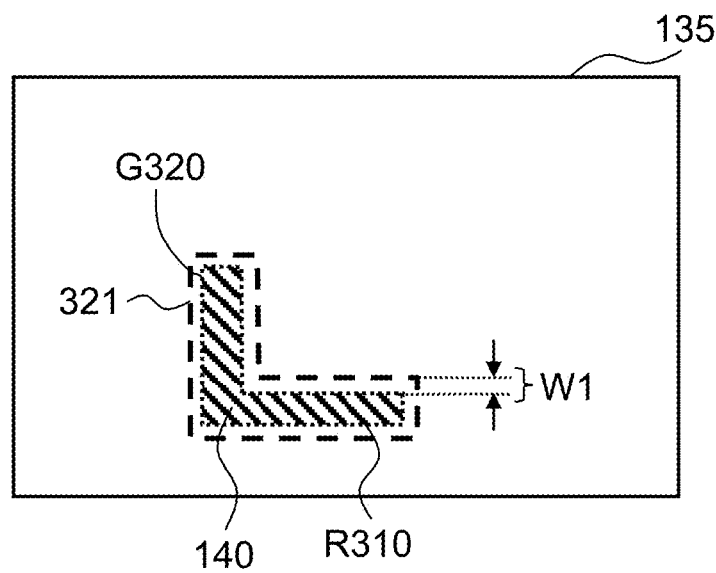
FIG. 11A is a diagram for describing the projection operation of a cutting aid line with a first cutting allowable range.
Figure 11B:
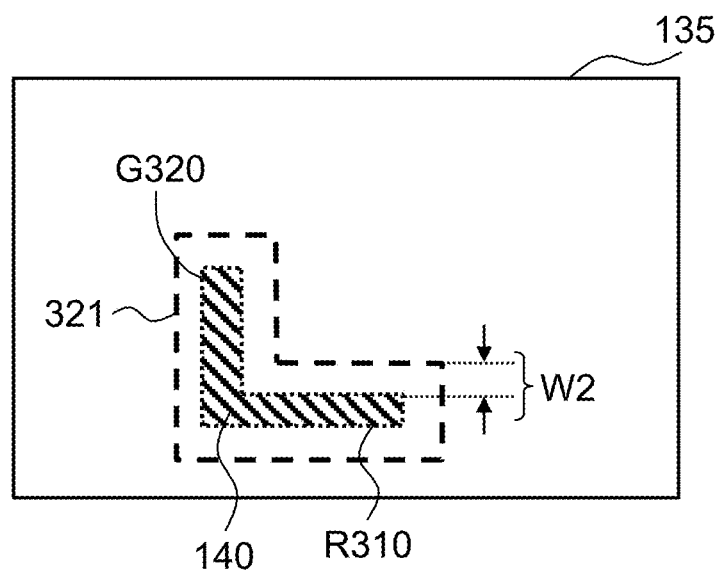
FIG. 11B is a diagram for describing the projection operation of a cutting aid line with a second cutting allowable range.

The projection operation of cutting aid line 321 according to the detection of affected part 140 will be described with reference to FIGS. 10, 11A, and 11B. FIG. 10 is a flowchart illustrating the projection operation of cutting aid line 321 according to the detection of affected part 140. FIGS. 11A and 11B are diagrams for describing the projection operation of cutting aid line 321 according to the detection of affected part 140.

It is supposed here that, before the start of surgery supported by surgery supporting system 100, a doctor plans a cutting position which is to be cut with a scalpel with allowance of a certain distance (hereinafter referred to as a "cutting allowable range") to affected part 140. It is also supposed that the doctor inputs the planned cutting allowable range to surgery supporting system 100 using an operation unit (not illustrated). For example, if the planned cutting allowable range is 2 centimeters, the doctor inputs information indicating the condition for the cutting aid line with the cutting allowable range of 2 centimeters to surgery supporting system 100. Control device 230 in surgery supporting system 100 stores the cutting allowable range into memory 240 on the basis of the input information.

The flowchart illustrated in FIG. 10 is started when the surgery supported by surgery supporting system 100 is started with the information indicating the condition for the cutting aid line being stored in memory 240.

Firstly, control device 230 reads the cutting allowable range or the like stored in memory 240 to acquire the condition for the cutting aid line (S400).

Then, control device 230 causes infrared camera 210 to capture the fluorescent image of infrared fluorescence 310 emitted from ICG in response to infrared excitation light 300 (S401). At that time, control device 230 specifies the coordinate of the area emitting infrared fluorescence from the captured image transmitted from infrared camera 210. Control device 230 also reads a shift correction amount from memory 240, and calculates a corrected coordinate obtained by correcting the specified coordinate based on the captured image transmitted from infrared camera 210 by the shift correction amount. In this way, control device 230 detects infrared fluorescence area R310 in affected part 140.

Then, control device 230 starts the irradiation of visible laser light 320 on the basis of the calculated corrected coordinate (S402). At that time, control device 230 calculates the position where cutting aid line 321 is to be projected on the basis of detected infrared fluorescence area R310 and the cutting allowable range acquired in step S400. Then, control device 230 controls MEMS mirror 221 such that laser scanning is performed on the area specified as affected part 140 and cutting aid line 321 is projected at the position away from the area specified as affected part 140 by the cutting allowable range.

Further, in the process in step S402, control device 230 adjusts the projection magnification on the basis of the distance information detected by TOF sensor 260. If the cutting allowable range is set as 2 centimeters, control device 230 controls MEMS mirror 221 such that cutting aid line 321 is projected at the position away from the area specified as affected part 140 by 2 centimeters. With this, cutting aid line 321 is projected at the position away from the area specified as affected part 140 by 2 centimeters around the area with the shape similar to the area. The projection of cutting aid line 321 will be described in more detail with reference to FIGS. 11A and 11B.

FIG. 11A illustrates surgical field 135 in the state in which the projection operation of cutting aid line 321 according to the detection of affected part 140 is performed in the case where first cutting allowable range W1 is set. FIG. 11B illustrates surgical field 135 in the state in which the projection operation of cutting aid line 321 according to the detection of affected part 140 is performed in the case where second cutting allowable range W2 is set. Second cutting allowable range W2 is supposed to be set larger than first cutting allowable range W1.

In FIGS. 11A and 11B, projection image G320 of visible light is projected on infrared fluorescence area R310 in affected part 140 emitting infrared fluorescence 310 in surgical field 135 according to the detection of infrared fluorescence 310 in the captured image. Control device 230 sets the irradiation position of visible laser light 320 for projecting cutting aid line 321 so as to enclose infrared fluorescence area R310 in surgical field 135 with a space of cutting allowable ranges W1 and W2 on the basis of the distance information detected by TOF sensor 260, as well as the irradiation position of projection image G320. Therefore, as illustrated in FIGS. 11A and 11B, surgery supporting system 100 can change the position on which cutting aid line 321 is projected according to the plan (cutting allowable range) of the cutting position planned by the doctor.

Notably, the cutting allowable range may be set beforehand on surgery supporting system 100 such as a small cutting size (e.g., 2 mm) or a large cutting size (e.g., 10 mm), or a doctor can set an arbitrary cutting allowable range beforehand or at any timing during a surgery.

In addition, cutting aid line 321 is not limited to a broken line illustrated in FIGS. 11A and 11B, and may be a solid line or a dotted line, or a line including dots and lines in combination, such as a one-dot chain line or a two-dot chain line. In the present exemplary embodiment, cutting aid line 321 is preferably other than a solid line for making it easy to identify cutting aid line 321 from projection image G320.

In addition, cutting aid line 321 may have a width by which a doctor can visually recognize cutting aid line 321 and can recognize a region to be cut. Preferably, cutting aid line 321 has a width from 2 mm to 5 mm inclusive, for example, and the line width of cutting aid line 321 may be changed in the same line as needed.

Returning to FIG. 10, control device 230 repeats the processes in S401 and S402 until the doctor or the like issues an end instruction through the operation unit (No in S403). When the end instruction is issued (Yes in S403), control device 230 ends the irradiation operation of visible laser light 320.

In the description of the flowchart in FIG. 10, the condition for cutting aid line 321 is cutting allowable ranges W1 and W2. However, the condition for cutting aid line 321 is not limited thereto, and it may be a threshold in a distribution of intensity of infrared fluorescence 310, for example. In this case, control device 230 extracts the boundary of the intensity distribution in the captured image on the basis of the captured image captured by infrared camera 210 and the threshold set as the condition for cutting aid line 321, and causes projector 220 to project cutting aid line 321 on the extracted boundary in the process in step S402. With this, in the case where, for the removal of a part of an organ, ICG is administered with blood flow or the like being limited so as to allow the portion to be removed to emit fluorescence, the doctor or the like can visually recognize the cutting position for the removal of the portion to be removed on the surface of the organ.

Further, as the condition for cutting aid line 321, both a threshold in the intensity distribution of infrared fluorescence and cutting allowable ranges W1 and W2 may be used, and cutting aid line 321 may be projected at the position away from the boundary of the intensity distribution in the captured image by cutting allowable ranges W1 and W2. Further, in the case where cutting aid line 321 is projected on the boundary of the intensity distribution of infrared fluorescence, control device 230 may determine the irradiation position through an image analysis of the captured image by infrared camera 210 without particularly using the distance information of TOF sensor 260.

6-3. Effects, Etc.

As described above, in the present exemplary embodiment, surgery supporting system 100 includes infrared camera 210, projector 220, and control device 230. Infrared camera 210 captures affected part 140. Projector 220 generates projection image G320 by visible light and projects the resultant on affected part 140. Control device 230 detects infrared fluorescence area R310 in affected part 140 emitting infrared fluorescence 310 on the basis of the captured image captured by infrared camera 210. Control device 230 causes projector 220 to project projection image G320 indicating detected infrared fluorescence area R310 and project cutting aid line 321, which is the projection image indicating the aid line, on the position corresponding to a predetermined condition on detected infrared fluorescence area R310.

With this, the irradiation of cutting aid line 321 can be performed in addition to the irradiation of the area specified as affected part 140 on the basis of the cutting allowable range input by the doctor prior to the start of surgery. According to this, the reproduction of the cutting position planned before the start of the surgery can be assisted, whereby the burden of the doctor can be reduced. Further, the time for preparation before the start of the surgery can be shortened.

Further, according to surgery supporting system 100, cutting aid line 321 is projected according to infrared fluorescence area R310 of affected part 140 detected based on the emission of infrared fluorescence 310. Therefore, the doctor or the like can visually recognize the aid line matching the position of affected part 140 in surgical field 135 in real time.

In surgery supporting system 100, the position on which cutting aid line 321 is projected may be set to the boundary of the intensity distribution on the basis of the intensity distribution of infrared fluorescence in the captured image.

In surgery supporting system 100, the predetermined condition may be cutting allowable ranges W1 and W2 indicating the space from detected infrared fluorescence area R310.

Surgery supporting system 100 may further include TOF sensor 260 that detects distance information indicating the distance from itself to affected part 140. Control device 230 may project cutting aid line 321 at the position spaced from detected infrared fluorescence area R310 by cutting allowable ranges W1 and W2 on the basis of the distance information detected by TOF sensor 260.

Notably, while cutting aid line 321 is projected at the position uniformly away from the area specified as affected part 140 by 2 centimeters when the cutting allowable range that is the predetermined condition is set as 2 centimeters in the above description, the configuration is not limited thereto. The position where cutting aid line 321 should be projected on the area specified as affected part 140 may be varied according to the cutting allowable range.

Further, in the above description, the irradiation for cutting aid line 321 can be turned on and off as necessary according to the operation by the doctor or the like during the irradiation of visible laser light 320 to the area specified as affected part 140. When the irradiation is turned off, the irradiation for cutting aid line 321 is not performed, and only the irradiation of visible laser light 320 to the area specified as affected part 140 is performed.

While the condition (cutting allowable range) for cutting aid line 321 is input prior to the start of surgery in the above description, the configuration is not limited thereto. Specifically, the condition for cutting aid line 321 may be changeable according to the operation by the doctor during the surgery.

In addition, projection image G320 and cutting aid line 321 may have different colors, brightnesses, or the like. For example, in the case where projection image G320 is blue, cutting aid line 321 is set to be green or red, which makes it easy to identify affected part 140 and the cutting position.

7. Projection Operation of Surgery Aid Information to Surrounding of Affected Part 7-1. Outline of Projection Operation of Surgery Aid Information A doctor performs surgery while confirming vital data of patient 130 as necessary. Vital data includes blood pressure, heart rate (pulse rate), oxygen concentration, and electrocardiogram. A doctor can perform surgery according to the change in condition of patient 130 by confirming vital data. A doctor also performs surgery while confirming an inspection image of patient 130 as necessary. Inspection image includes an image with MRI (Magnetic Resonance Imaging), an image with CT (Computed Tomography), and a radiographic image. A doctor can perform surgery according to the inspection result of patient 130 by confirming the inspection image. A doctor also performs surgery while confirming a memo indicating the procedure of the surgery or notes for the surgery according to need.

Figure 12A:
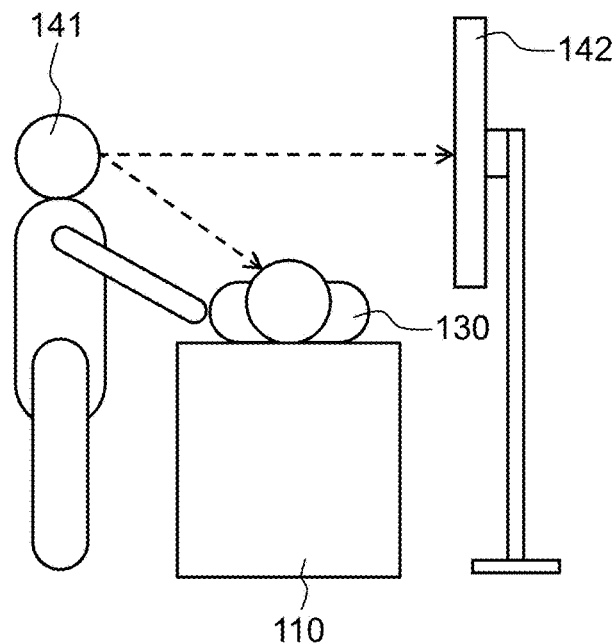
FIG. 12A is a view illustrating a state of conventional surgery.

As described above, a doctor performs surgery while confirming surgery aid information such as vital data, an inspection image, and a procedure of surgery, as necessary. FIG. 12A is a view illustrating a state of conventional surgery. Surgery aid information is displayed on monitor 142. Doctor 141 performs surgery on patient 130 while confirming surgery aid information displayed on monitor 142. At that time, doctor 141 performs surgery while moving his/her eye to monitor 142 and patient 130, which increases a burden of doctor 141 and increases time for confirmation.

In view of this, the inventor of the present disclosure has conceived of projecting surgery aid information 151 around affected part 140 as associated information in addition to the projection of a visible-light image onto an area specified as affected part 140. With this, the eye movement of a doctor or the like can be reduced during surgery. Thus, the burden on the doctor or the like can be reduced, and the confirmation time can be reduced.

7-2. Detail of Projection Operation of Surgery Aid Information

Figure 12B:
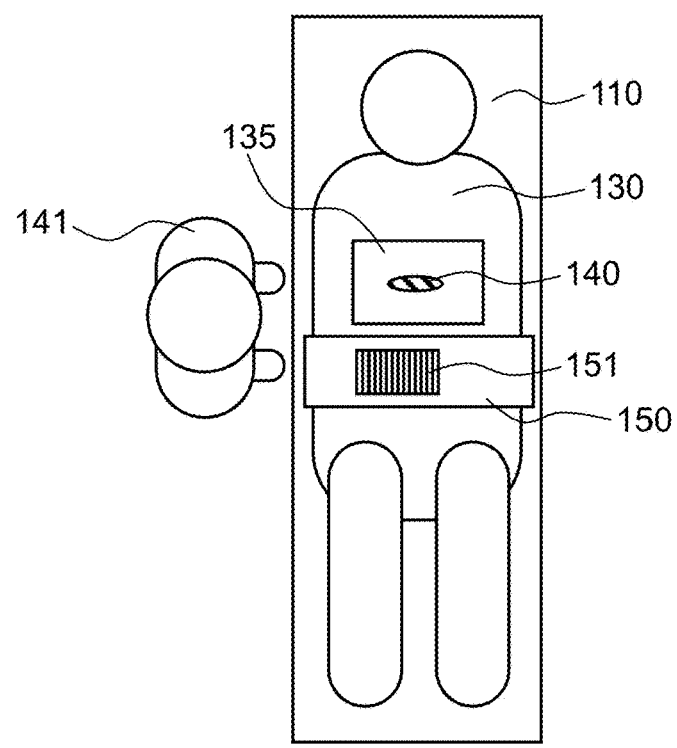
FIG. 12B is a view for describing projection of surgery aid information onto the surrounding of an affected part.
Figure 13A:
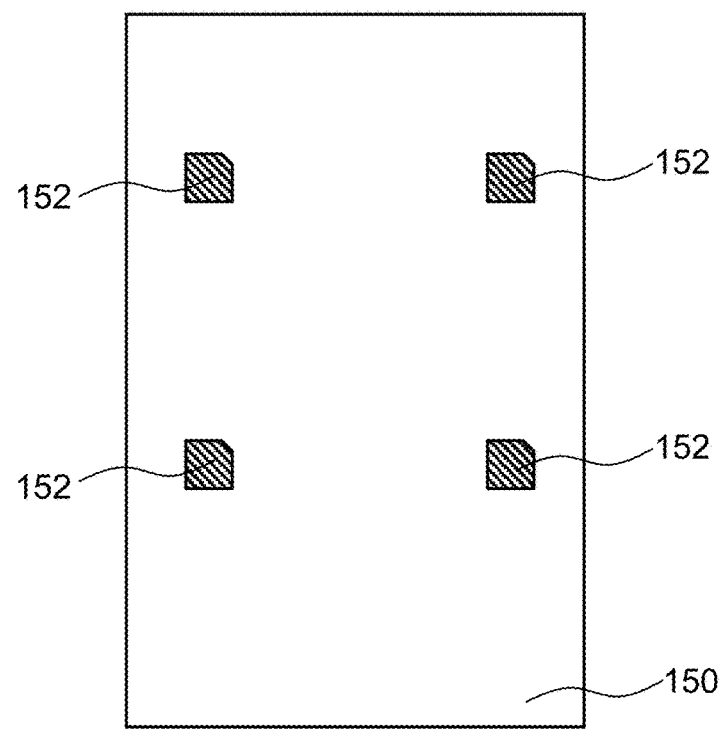
FIG. 13A is a top view of an auxiliary screen material on which surgery aid information is not projected.
Figure 13B:
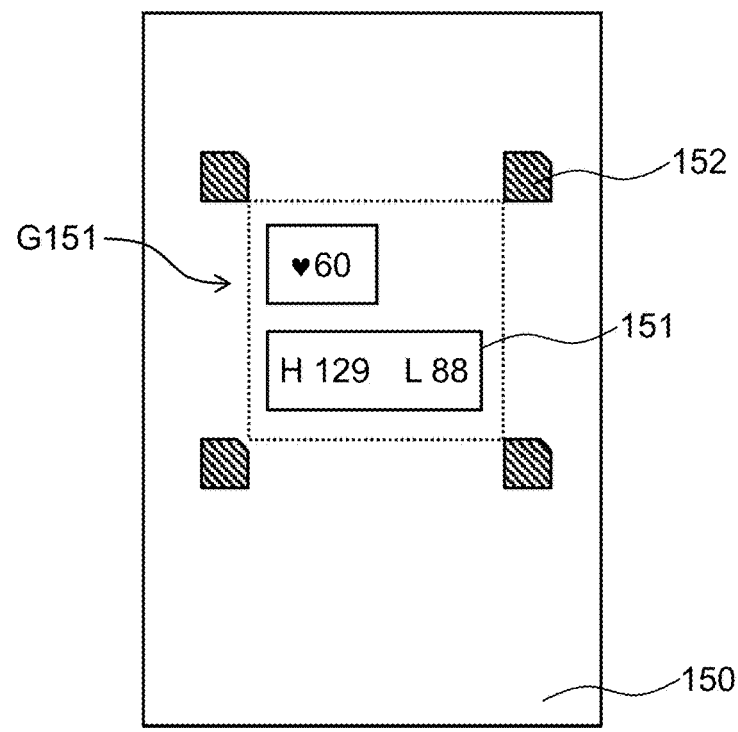
FIG. 13B is a top view of an auxiliary screen material on which surgery aid information is projected.

The projection of surgery aid information onto the surrounding of affected part 140 will be described with reference to FIGS. 12B, 13A, and 13B. FIG. 12B is a view for describing projection of surgery aid information 151 onto the surrounding of affected part 140. FIGS. 13A and 13B are views for describing the projection of surgery aid information 151 onto an auxiliary screen material 150.

Control device 230 in surgery supporting system 100 is communicatively connected to a medical device (not illustrated) from which various vital data is acquired. With this, control device 230 acquires vital data required for surgery in real time from the communicatively-connected medical device.

Further, inspection image data of patient 130 and a memo of the procedure of the surgery are previously stored in memory 240 through the operation on the operation unit by doctor 141 prior to the start of the surgery. Thus, control device 230 reads and acquires the inspection image data and the memo of the procedure of the surgery necessary for the surgery from memory 240.

FIG. 12B is a view illustrating the state of the projection of surgery aid information 151 according to the present exemplary embodiment. Prior to the start of the surgery, doctor 141 or the like places auxiliary screen material 150 on which surgery aid information 151 is projected around affected part 140 of patient 130 as illustrated in FIG. 12B. Any material may be used for auxiliary screen material 150, so long as it can display a projection image. Further, a material having any shape and size may be used for auxiliary screen material 150, so long as it has a size placeable around affected part 140. In the example in FIG. 12B, auxiliary screen material 150 is placed at the right of affected part 140 viewed from doctor 141. However, the placing position is not limited thereto. Auxiliary screen material 150 may be placed at any position around affected part 140 according to the dominant arm of the doctor using surgery supporting system 100, easiness in confirmation, or the surgical matter.

FIG. 13A is a top view of auxiliary screen material 150 on which surgery aid information is not projected. As illustrated in FIG. 13A, markers 152 are formed on the top surface of auxiliary screen material 150. Markers 152 are positioned on auxiliary screen material 150 as a reference indicating the area on which surgery aid information 151 is displayed on auxiliary screen material 150.

A camera (not illustrated) is connected to control device 230 of surgery supporting system 100. The camera captures an image of markers 152 formed on auxiliary screen material 150. The camera transmits the captured image of markers 152 to control device 230. The correspondence relation in coordinates between the captured area in the captured image by the camera and the projection area of surgery aid information by visible-light laser 222 is stored in memory 240 in advance. Control device 230 specifies the area on which surgery aid information 151 is to be projected from the correspondence relation stored in memory 240 and the detection result of the positions of markers 152 from the transmitted captured image. Then, control device 230 controls MEMS mirror 221 such that surgery aid information 151 is projected onto the specified area. Thus, projection image G151 indicating surgery aid information 151 is projected on the top surface of auxiliary screen material 150 as illustrated in FIG. 13B.

Surgery supporting system 100 projects projection image G151 of surgery aid information 151 on auxiliary screen material 150 along with projection image G320 (see FIG. 2B) projected on infrared fluorescence area R310 specified as affected part 140. With this, the eye movement of the doctor can be reduced during the surgery. Thus, the burden on doctor 141 can be reduced, and the confirmation time can be reduced, whereby the surgery can be supported.

While surgery aid information 151 is projected on auxiliary screen material 150 in the above description, it is not limited thereto. Surgery aid information 151 may be directly projected on the surface of the body of patient 130, not on auxiliary screen material 150. In this case, markers 152 may be formed on the surface of the body of patient 130.

While the camera for capturing an image of markers 152 is used in the above description, the configuration is not limited thereto. For example, an image of markers 152 may be captured by infrared camera 210. In this case, markers 152 are made of a material formed by applying ICG thereon, kneading ICG therein, or injecting ICG therein, for example. With this, images of affected part 140 and markers 152 can be captured only by infrared camera 210.

While the area on which surgery aid information 151 is to be projected is specified by using markers 152 in the above description, the configuration is not limited thereto. Specifically, the area on which surgery aid information 151 is to be projected may be specified without using markers 152. For example, surgery aid information 151 may be projected at the position away, by the distance in the direction as set by the doctor beforehand, from the position of affected part 140 to which visible laser light 320 is emitted.

For example, it is supposed to be set beforehand such that surgery aid information 151 is projected at the position away from the rightmost end of the area specified as affected part 140 to the right by 20 centimeters as viewed from doctor 141. In this case, control device 230 controls MEMS mirror 221 such that surgery aid information 151 is projected on the position set beforehand with respect to the area specified as affected part 140. Thus, surgery aid information 151 can be projected on an arbitrary position which is easy to be confirmed by doctor 141. It is to be noted that control device 230 may calculate the position on which surgery aid information 151 is to be projected in surgical field 135 on the basis of distance information detected by TOF sensor 260.

7-3. Effects, Etc.

As described above, in the present exemplary embodiment, surgery supporting system 100 includes infrared camera 210, projector 220, and control device 230. Infrared camera 210 captures affected part 140. Projector 220 generates projection image G320 by visible light and projects the resultant on affected part 140. Control device 230 controls the projection operation of projector 220 on the basis of the captured image captured by infrared camera 210. Control device 230 controls projector 220 such that projection image G320 indicating captured affected part 140 is projected and projection image G151 indicating surgery aid information 151, which is the information concerning the surgery to affected part 140, is projected in the vicinity of affected part 140.

Thus, projection image G151 is projected in the vicinity of affected part 140, whereby an eye movement of a doctor or the like from affected part 140 when a doctor or the like confirms surgery aid information 151 can be decreased to reduce a burden on the doctor during the surgery.

Further, surgery supporting system 100 may further include auxiliary screen material 150 that is disposed near affected part 140 and has markers 152. In this case, control device 230 projects projection image G151 on auxiliary screen material 150 by using the positions of markers 152 as a reference. Surgery supporting system 100 may further include a camera for capturing an image of markers 152, or may capture an image of markers 152 by infrared camera 210.

Surgery supporting system 100 may further include memory 240 that stores surgery aid information 151. Further, control device 230 may acquire surgery aid information 151 through communication with an external device.

Surgery supporting system 100 may further include a distance detection unit such as TOF sensor 260 that detects distance information indicating the distance from itself to affected part 140. Control device 230 may cause projector 220 to project surgery aid information 151 at the position away from affected part 140 by a predetermined distance on the basis of the detected distance information. Control device 230 may also cause projector 220 to project surgery aid information 151 on almost a flat area near affected part 140 on the basis of the detected distance information. The distance detection unit may output a distance image as distance information, for example.

8. Monitoring of Use Height of Imaging Irradiation Device

8-1. Outline of Monitoring Operation of Use Height

In surgery supporting system 100 illustrated in FIG. 1, use heights of imaging irradiation device 200 and surgical bed 110 are adjusted at the start of surgery such that the body axis of patient 130 is located at the position 1000 mm away from the lower surface of imaging irradiation device 200 according to the height allowable range of 1000 mm±300 mm based on the focal length of infrared camera 210, for example. However, during the surgery, patient 130 may be turned over according to the matter of the surgery or the location of imaging irradiation device 200 may be changed due to a change in operators, so that the use heights of imaging irradiation device 200 and surgical bed 110 are changed.

According to the present invention, a distance detection unit is provided to imaging irradiation device 200 so as to monitor the use height of imaging irradiation device 200 during surgery, whereby patient 130 can be turned over or the height of the surgical bed can be adjusted according to the matter of the surgery within an allowable range of the use height. On the other hand, when the use height is outside the allowable range, a warning is issued to avoid false recognition of a user such as a doctor. Further, safety during surgery can be ensured under the control such that a projection image is not projected when the use height is outside the allowable range.

In the present exemplary embodiment, TOF sensor 260 that radiates infrared detection light 330 with wavelength of 850 nm to 950 nm is used as the distance detection unit. Infrared detection light 330 radiated from TOF sensor 260 is reflected on the surface of the body of patient 130, and then, returns to TOF sensor 260 to be received. In this case, infrared detection light 330 reflected on the surface of the body of patient 130 reaches not only TOF sensor 260 but also infrared camera 210.

The present invention includes a configuration for controlling TOF sensor 260 and infrared excitation light source 250 or visible-light laser 222 in an opposite way in order to monitor a safe use height while implementing a surgery support with the detection of infrared fluorescence 310.

8-2. Detail of Monitoring Operation of Use Height

The detail of the monitoring operation of a use height will be described below.

8-2-1. With Regard to Process Flow

Figure 14:
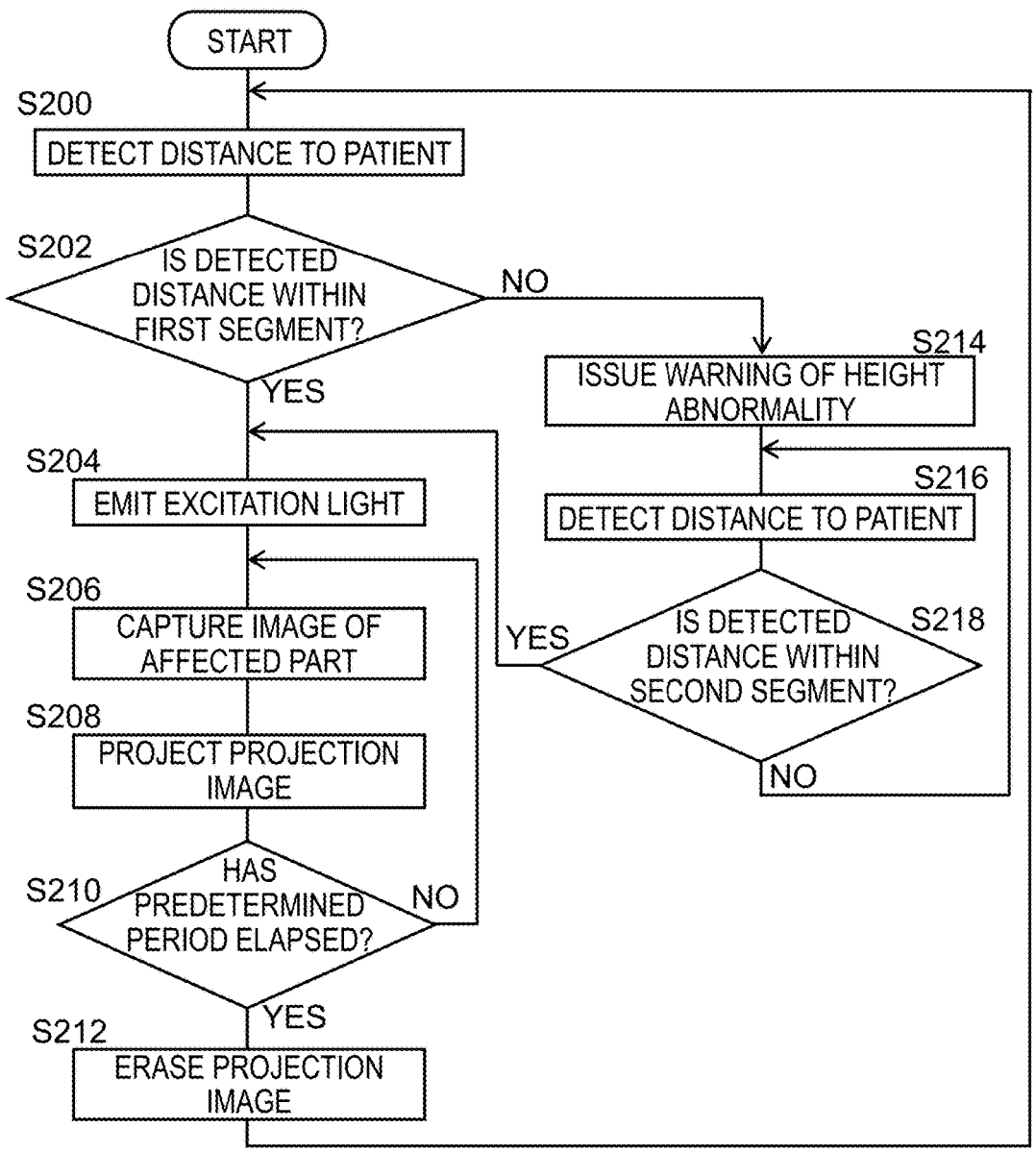
FIG. 14 is a flowchart illustrating the process flow in a monitoring operation of a use height.
Figure 15A:
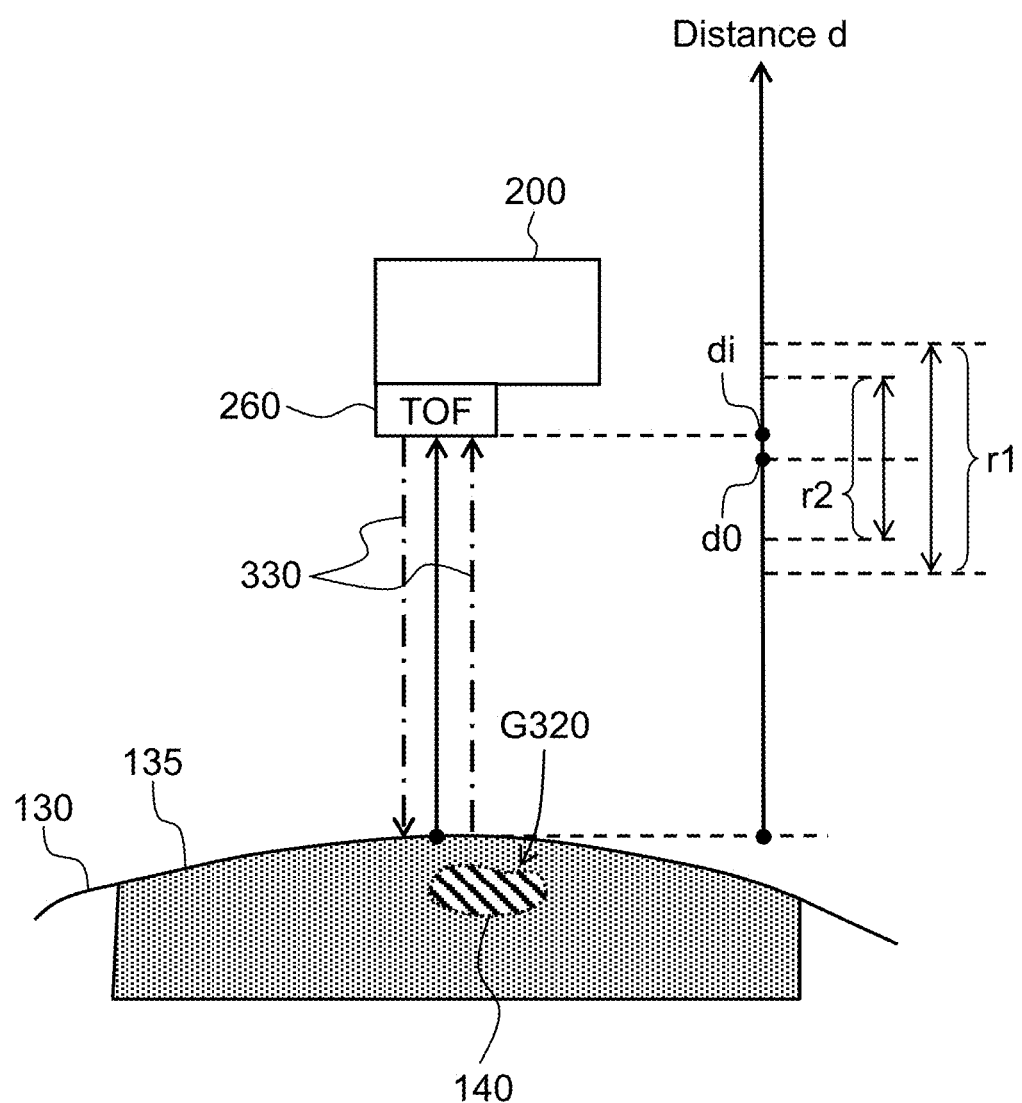
FIG. 15A is a view for describing the monitoring operation when a use height falls within an allowable range.
Figure 15B:
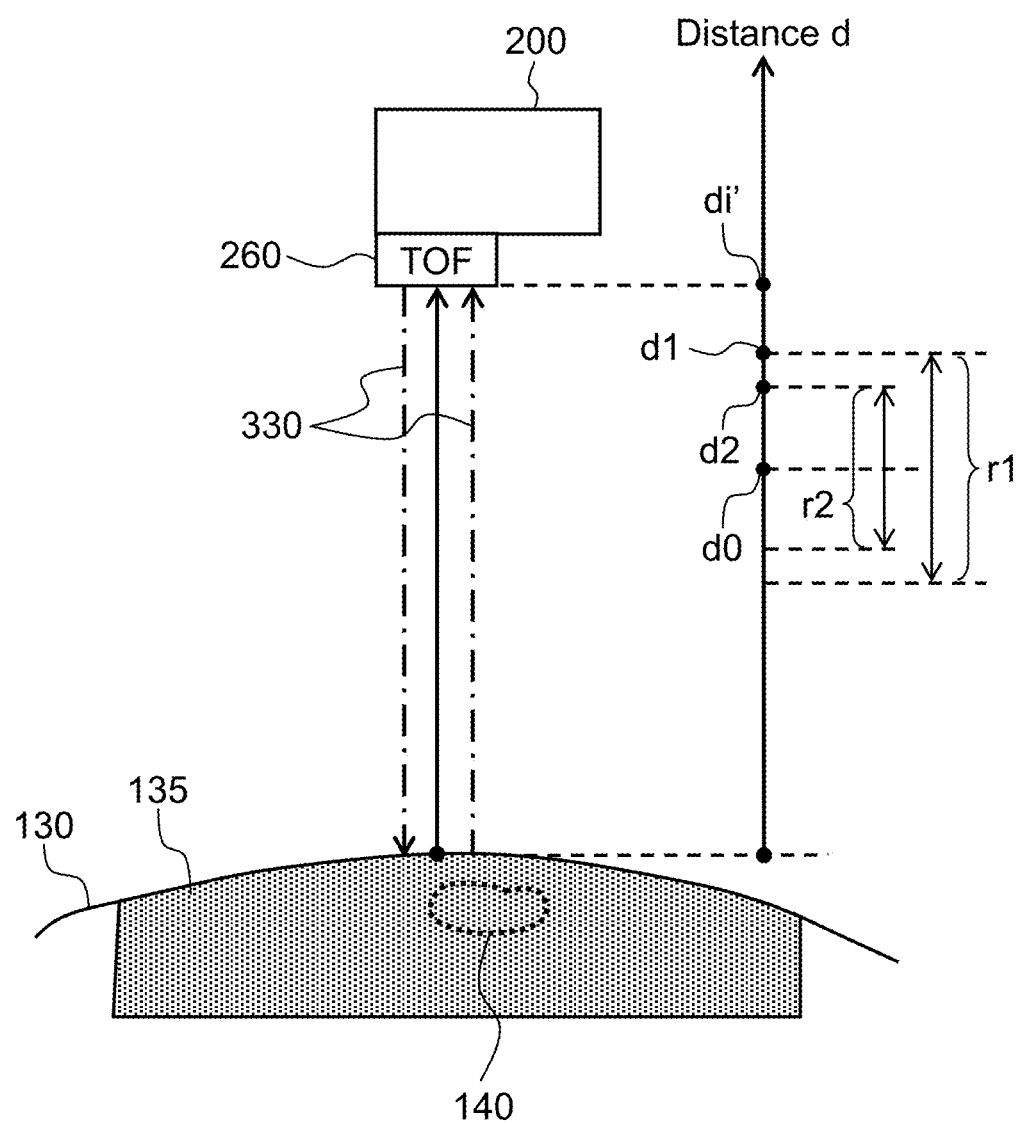
FIG. 15B is a view for describing the monitoring operation when a use height falls outside an allowable range.

Firstly, the process flow in the monitoring operation of the use height in surgery supporting system 100 will be described with reference to FIGS. 14, 15A, and 15B. FIG. 14 is a flowchart illustrating the process flow in a monitoring operation of a use height. FIGS. 15A and 15B are views for describing the monitoring operation of a use height. This flow is executed by control device 230 in surgery supporting system 100 (see FIG. 1).

In the flowchart in FIG. 14, TOF sensor 260 firstly radiates infrared detection light 330 and receives its reflection wave to detect distance di from itself to patient 130 under the control of control device 230 (S200) as illustrated in FIG. 15A. In step S200, TOF sensor 260 radiates infrared detection light 330 only during predetermined period T1 (see FIG. 16). TOF sensor 260 outputs the detected distance information to control device 230.

Then, control device 230 determines whether or not detected distance di falls within predetermined first segment r1 on the basis of the distance information from TOF sensor 260 (S202). First segment r1 indicates the allowable range of the distance between imaging irradiation device 200 and affected part 140 by which surgery supporting system 100 is normally operable. In the present exemplary embodiment, first segment r1 is set to be 1000±300 mm with d0 being specified as a standard distance that is 1000 mm.

When determining that detected distance di is di', and di' is outside first segment r1 as illustrated in FIG. 15B (NO in S202), control device 230 issues a warning indicating that the use height is abnormal (S214). The warning in step S214 may be generated such that a message or a warning sound indicating that the use height is in the "abnormal state" is issued from a speaker (not illustrated). Notably, in step S214, a projection image is not projected on affected part 140 as illustrated in FIG. 15B.

Then, after the lapse of period T1, control device 230 causes TOF sensor 260 to detect distance di from itself to patient 130 as in the process in step S200 (S216).

Then, control device 230 determines whether or not detected distance di falls within predetermined second segment r2 (S218). Second segment r2 indicates that surgery supporting system 100 is located at the position where it can be returned from the abnormal state. Second segment r2 is shorter than first segment r1, and r2 is 1000±200 mm, for example.

When determining that detected distance di is outside second segment r2 (NO in S218), control device 230 repeatedly performs the process in step S216 in a predetermined cycle. On the other hand, when determining that detected distance di falls within second segment r2 (YES in S218), control device 230 sequentially performs the processes in step S204 and subsequent steps.

When determining that detected distance di falls within first segment r1 as illustrated in FIG. 15A (YES in S202), control device 230 controls infrared excitation light source 250 (see FIG. 1) such that infrared excitation light 300 is emitted to surgical field 135 (S204).

During the irradiation of infrared excitation light 300, control device 230 causes infrared camera 210 to capture affected part 140 in surgical field 135 (S206). Control device 230 causes projector 220 to project projection image G320 of visible light on the basis of the image captured in the process of step S206 (S208). The processes in steps S202, S204, and S206 are performed similarly to the above-mentioned basic projection operation in surgery supporting system 100 (see FIG. 2A and FIG. 2B).

Then, control device 230 determines whether or not predetermined period T2 has elapsed after the start of the irradiation of infrared excitation light 300 in step S204 (S210). Control device 230 repeatedly executes the processes in steps S206 and S208 in a predetermined cycle (e.g., 1/60 second) until period T2 has elapsed (NO in S210).

After the lapse of period T2 (YES in S210), control device 230 causes infrared excitation light source 250 to stop the irradiation of infrared excitation light 300, and causes projector 220 to erase projection image G320 (S212). After the process in step S212, control device 230 returns to the process in step S200.

It is to be noted that, since TOF sensor 260 detects the distance using infrared light, control device 230 stops other light sources in step S212 before returning to step S200 to prevent influence on the distance detection. However, if projector 220 has a configuration of using a light source having no infrared light component, which configuration has no influence on the distance detection, control device 230 may only cause infrared excitation light source 250 to stop the irradiation of infrared excitation light 300 in step S212.

According to the above processes, a warning is generated in the process in S214 when the use height of imaging irradiation device 200 is outside the allowable range, whereby a user such as a doctor can recognize that the use height of imaging irradiation device 200 is outside the allowable range. Further, the distance detection process in step S200 is performed after the process in step S212 to control TOF sensor 260 and projector 220 or the like in an opposite way, whereby the distance detection can be implemented without causing malfunction of surgery supporting system 100.

8-2-2. With Regard to Opposite Control

Figure 16:
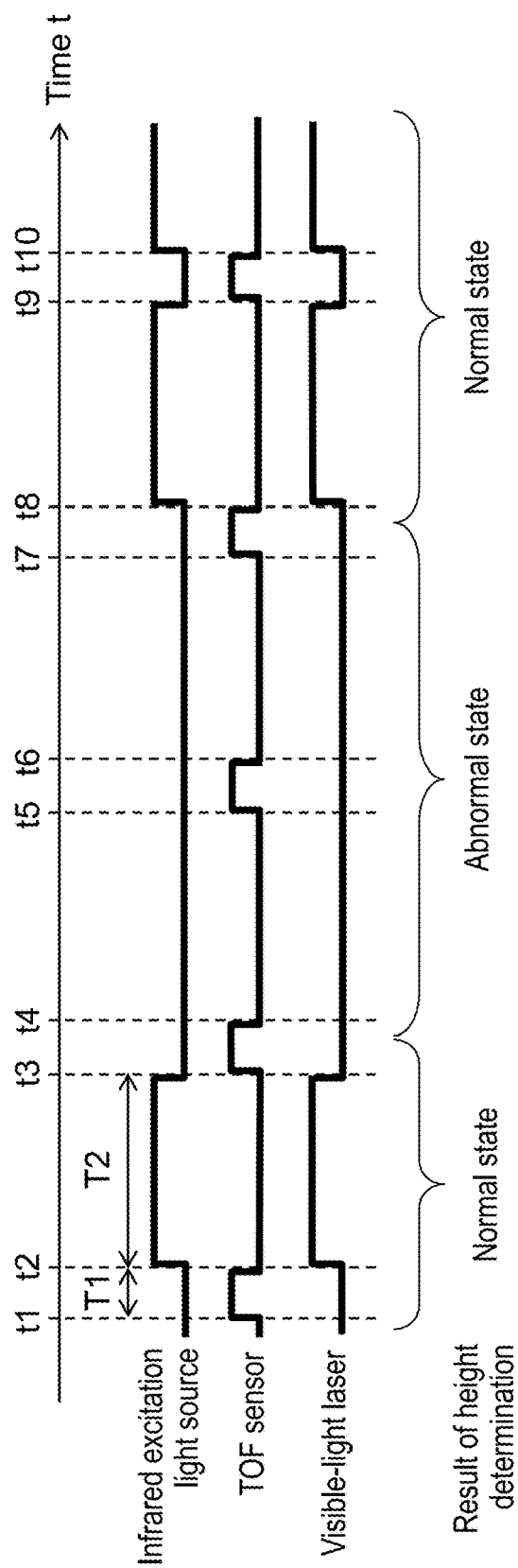
FIG. 16 is a timing chart for describing operations of an infrared excitation light source, a TOF sensor, and a visible-light laser.

The opposite control in monitoring the use height of imaging irradiation device 200 will be described below in detail with reference to FIGS. 14 to 16. FIG. 16 is a timing chart for describing the operation of infrared excitation light source 250, TOF sensor 260, and visible-light laser 222 according to a height detection result. The horizontal axis in FIG. 16 indicates a time axis. In FIG. 16, a low level in each chart indicates an unlit state, while a high level indicates a lit state.

Here, the "lit state" indicates that a power source of each of infrared excitation light source 250, TOF sensor 260, and visible-light laser 222 is turned on. On the other hand, the "unlit state" indicates that the power source of each of infrared excitation light source 250, TOF sensor 260, and visible-light laser 222 is turned off.

Control device 230 periodically executes the height (distance) determination by TOF sensor 260 during the operation of surgery supporting system 100. Specifically, as illustrated in FIG. 16, control device 230 executes the determination process in steps S200 and S202 or in steps S216 and S218 in FIG. 14 during period T1 from times t1 to t2, during period T1 from times t3 to t4, during period T1 from times t5 to t6, during period T1 from times t7 to t8, during period T1 from times t9 to t10, . . . . In this case, TOF sensor 260 is in a lit state of radiating infrared detection light 330. Control device 230 causes infrared excitation light source 250 and visible-light laser 222 to be an unlit state during each period T1 in which TOF sensor 260 performs height determination. That is, the opposite control for bringing infrared excitation light source 250 and visible-light laser 222 into the unlit state during the lit state of TOF sensor 260 is performed. Period T1 from times t1 to t2, period T1 from times t3 to t4, period T1 from times t5 to t6, period T1 from times t7 to t8, and period T1 from times t9 to t10 are all short periods such as 10 msec to 100 msec. Therefore, these periods are hardly sensed by a human. Therefore, even if the opposite control is performed during the period of height determination, surgery supporting system 100 can make a human feel as if the projection image by visible laser light 320 is continuously displayed.

It is supposed here that, during period T1 from times t1 to t2, distance di indicated by the detection result of TOF sensor 260 falls within first segment r1 (=1000 mm±300 mm) indicating the height allowable range as illustrated in FIG. 15A. In this case, control device 230 determines that the use height is in the "normal state" as the result of the height determination in step S202 in FIG. 14. Then, control device 230 brings both infrared excitation light source 250 and visible-light laser 222 into the lit state during subsequent period T2 from times t2 to t3. Thus, during period T2 from times t2 to t3, projection image G320 is projected onto affected part 140 to normally support the surgery as usual.

Next, it is supposed that, during period T1 from times t3 to t4, distance di indicated by the detection result of TOF sensor 260 is di' which is outside height allowable range r1 (=1000 mm±300 mm) as illustrated in FIG. 15B. In this case, control device 230 determines that the use height is in the "abnormal state" as the result of the height determination in step S202. In this case, the projection image is likely to be inaccurately projected, so that it is considered that it had better not to continue the surgery support from the viewpoint of safety. Then, control device 230 keeps both infrared excitation light source 250 and visible-light laser 222 into the unlit state even during subsequent period T2 from times t4 to t5. Thus, during period T2 from times t4 to t5, a projection image which may be inaccurate is not displayed, and the surgery support can be stopped with safety being prioritized.

It is supposed that, during subsequent period T1 from times t5 to t6, distance di indicated by the detection result of TOF sensor 260 is between distance d1 at one end of first segment r1 and distance d2 at one end of second segment r2 (e.g., 1250 mm). In this case, imaging irradiation device 200 falls within the height allowable range, but since the use height is close to the limit of the height allowable range, there is a fear that the use height immediately falls outside the height allowable range. In view of this, a hysteresis range is formed in second segment r2 smaller than first segment r1, and the determination process in step S218 in FIG. 14 is performed. With this, when distance di is between first distance d1 and distance d2, it is determined to be in the "abnormal state", so that the operation similar to that during period T2 from times t4 to t5 is performed to ensure safety even during period T2 from times t6 to t7.

Next, it is supposed that, during period T1 from times t7 to t8, distance di indicated by the detection result of TOF sensor 260 falls within second segment r2 (=1000 mm±200 mm) indicating the height allowable range with the hysteresis range. In this case, control device 230 determines that the use height is in the "normal state" as the result of the height determination in step S218. Then, control device 230 brings both infrared excitation light source 250 and visible-light laser 222 into the lit state during subsequent period T2 from times t8 to t9. Thus, during period T2 from times t8 to t9, projection image G320 is projected onto affected part 140 as normal, and the surgery support can be performed again.

Notably, a margin period in which TOF sensor 260 as well as infrared excitation light source 250 and visible-light laser 222 are in the unlit state may be formed at the switching timing of t1, t3, t5, t7, t9, . . . . With this, erroneous detection of infrared detection light 330 at the switching timing can be prevented. In addition, a margin period may be formed at the switching timing of t2, t4, t6, t8, t10, . . . .

8-3. Effects, Etc.

As described above, in the present embodiment, surgery supporting system 100 includes infrared camera 210, projector 220, TOF sensor 260, and control device 230. Infrared camera 210 captures affected part 140. Projector 220 generates projection image G320 on the basis of the captured image of affected part 140 and projects the resultant image onto affected part 140. TOF sensor 260 detects the distance from itself to affected part 140. Control device 230 controls the operations of infrared camera 210 and projector 220. Control device 230 determines whether or not the distance detected by TOF sensor 260 falls within first segment r1. When the distance detected by TOF sensor 260 falls within first segment r1, control device 230 generates projection image G320 and projects this image onto affected part 140.

According to surgery supporting system 100 described above, when the distance detected by TOF sensor 260 falls within first segment r1, projection image G320 is generated and projected on affected part 140 even if the imaging position of affected part 140 is changed. Thus, safety in projecting projection image G320 can be ensured.

Further, control device 230 generates a predetermined warning when the distance detected by TOF sensor 260 is outside first segment r1.

Thus, surgery supporting system 100 teaches a doctor or the like that the distance from TOF sensor 260 to affected part 140 exceeds first segment r1, and thus is capable of ensuring safety while in use. Accordingly, surgery supporting system 100 can be easy to be used by a user such as a doctor.

Further, when the distance detected by TOF sensor 260 is outside first segment r1, projection image G320 may not be projected on affected part 140 in place of or in addition to the configuration of generating a predetermined warning. With this, the projection of projection image G320 which may be inaccurate because of the detected distance exceeding first segment r1 is stopped in surgery supporting system 100, whereby safety during surgery can be enhanced.

In addition, infrared camera 210 may receive infrared fluorescence 310 having a first spectrum and capture an image of affected part 140. TOF sensor 260 may radiate infrared detection light 330 having a second spectrum to detect the distance from itself to affected part 140. In this case, TOF sensor 260 radiates infrared detection light 330 during first period T1, and does not radiate infrared detection light 330 during second period T2 different from first period T1. Control device 230 does not allow the projection of projection image G320 during first period T1 and allows the projection of projection image G320 during second period T2. Thus, the distance from TOF sensor 260 to affected part 140 can be detected without causing malfunction of surgery supporting system 100.

In the above description, infrared excitation light source 250 and visible-light laser 222 are both brought into the unlit state when the determination of the "abnormal state" is made. However, the configuration is not limited thereto. One of infrared excitation light source 250 and visible-light laser 222 may be turned off. When infrared excitation light source 250 is brought into the unlit state, infrared fluorescence 310 is not emitted from ICG. Therefore, control device 230 cannot specify an area of affected part 140, so that visible laser light 320 is not radiated even if visible-light laser 222 is in the lit state. Further, when visible-light laser 222 is brought into the unlit state, visible laser light 320 is never emitted.

In addition, when the determination of the "abnormal state" is made, control device 230 may cause infrared camera 210 not to capture an image in place of or in addition to the control of infrared excitation light source 250 and visible-light laser 222. Further, control device 230 may cause MEMS mirror 221 not to generate projection image G320. That is, control device 230 may control any of components in surgery supporting system 100 in order that projection image G320 based on the capturing result of infrared camera 210 is not projected.

Further, the example of the warning operation for issuing, from a speaker, a message or a warning sound indicating that the use height is in the "abnormal state" when the determination of the "abnormal state" is made has been described above. However, the warning operation is not limited thereto. The warning may be an operation for outputting information indicating that the distance to a subject such as affected part 140 is outside a predetermined segment range. For example, when the use height is determined to be in the "abnormal state", a user such as a doctor may be notified that it is in the "abnormal state". The method for notifying the "abnormal state" may be such that visible-light laser 222 is changed to the one having other wavelength, and visible laser light 320 may be emitted with its color being changed. Further, a warning may be issued by projecting a projection image including a text message that indicates the "abnormal state".

In the above description, projection image G320 based on the capturing result of infrared camera 210 is erased upon generating a warning. However, the configuration is not limited thereto. For example, a projection image based on the capturing result of infrared camera 210 may be used as a warning. For example, a projection image based on the capturing result of infrared camera 210 may be projected with its color being changed or may be projected while flashing.

In the above description, TOF sensor 260 uses infrared detection light 330 with a spectrum superimposed on the spectrum of infrared fluorescence 310. However, it is not limited thereto. For example, TOF sensor 260 may radiate detection light not superimposed on the spectrum of infrared fluorescence 310 to perform distance detection. In this case, a wavelength filter that blocks the spectrum of infrared fluorescence 310 may be provided on a light-emitting unit of TOF sensor 260, for example. Here, a wavelength band with wavelength of 850 nm to 950 nm has high atmospheric transmittance, so that the distance detection is easy to be performed. Therefore, the efficiency in the distance detection can be enhanced by performing the opposite control described above without using a wavelength filter.

In the above description, a use height is monitored with the distance detection by TOF sensor 260. However, it is not limited thereto. For example, the distance between imaging irradiation device 200 and a subject such as affected part 140 may be monitored with the distance detection by TOF sensor 260 in order that surgery supporting system 100 can appropriately operate even when the direction of imaging irradiation device 200 is changed.

Further, it has been described with reference to FIG. 16 that the state transition of each of infrared excitation light source 250 and visible-light laser 222 between the "lit state" and the "unlit state" is implemented by switching the power source of the light source between an on state and an off state. However, the configuration is not limited thereto. The "lit state" and the "unlit state" may be implemented by switching an on state and an off state for light-shielding by light-shielding means, even if the power source of the light source is kept into the on state.

Other Exemplary Embodiments

The first exemplary embodiment has been described above as an illustration of the technology disclosed in the present application. However, the technology in the present disclosure is not limited to this, and can be applied to embodiments in which various changes, replacements, additions, omissions, etc., are made as necessary. Furthermore, a new embodiment can be formed by combining the components described in the first exemplary embodiment.

The other exemplary embodiments will be described below.

The first exemplary embodiment describes as one example a medical application such as surgery. However, the present invention is not limited thereto. For example, the present invention is applicable to the case where work is performed on an object of which state change cannot be confirmed by visual observation in, for example, a construction site, a mining site, a building site, or a material processing plant.

Specifically, in place of the medical device according to the first exemplary embodiment, a fluorescent material may be applied on, kneaded into, or injected into an object of which state change cannot be confirmed by visual observation, and the resultant object may be used as a target to be captured by infrared camera 210, in a construction site, a mining site, a building site, or in a material processing plant, for example. Not a portion emitting light but a portion generating heat may be detected by a heat sensor, and only this portion or only the boundary may be scanned.

The first exemplary embodiment describes using a laser light source. However, the configuration is not limited thereto for projection of a cutting aid line or projection of surgery aid information. That is, a cutting aid line or surgery aid information may be projected using a light source other than a laser light source.

The first exemplary embodiment describes that a cutting aid line or surgery aid information is projected using visible-light laser 222 that is the same as a light source used for the projection to an area specified as an affected part. However, the configuration is not limited thereto. The cutting aid line or surgery aid information may be projected using a light source different from the light source used for the projection to the area specified as the affected part. However, it is obvious that such light source is controlled to perform projection corresponding to the projection to the area specified as the affected part.

In the first exemplary embodiment, TOF sensor 260 is used as the distance detection unit. However, it is not limited thereto. For example, a sensor may be used that radiates infrared detection light having a known pattern such as a random dot pattern and measures distance on the basis of the shift with the pattern of its reflection wave. In this case, the distance detection unit can detect distance information as a distance image indicating distance to each dot in a two-dimensional area.

Further, the first exemplary embodiment describes projection image G320 of a monochrome uniform image by visible-light laser 222. The projection image projected by the projector is not limited thereto, and a gray-scaled projection image or a full-color projection image may be projected, or an arbitrary image may be projected.

The usable range of surgery supporting system 100 according to the present exemplary embodiment is the range where infrared camera 210 can capture an image and a range where projector 220 can project an image. In addition, the range where projector 220 can project an image is the range including the range where the associated information (cutting aid line 321, surgery aid information 151, etc.) described above can be projected, as well as the range where infrared camera 210 can capture an image. However, it is not limited thereto, so long as surgery supporting system 100 can be used in surgical field 135 without any problems.

In addition, in the present exemplary embodiment, the optical path of visible laser light 320 and the optical path of infrared fluorescence 310 are the same as illustrated in FIG. 1 as described above. However, they may be different from each other, that is, infrared camera 210 and projector 220 may be located on different positions and may have different optical paths.

Notably, if the optical paths are different from each other, in the case where the position of patient 130 is changed, an image is projected on the basis of the shift correction amount stored in memory 240 as described above, and besides, the shape of an image to be projected by projector 220 needs to be corrected from an image captured by infrared camera 210, because the position of infrared camera 210 and the position of projector 220 are different from each other.

Specifically, when the position of patient 130 is changed, a difference in an amount of change is generated between the distance from infrared camera 210 to patient 130 and the distance from projector 220 to patient 130. That is, due to the movement of patient 130, the distance between infrared camera 210 and patient 130 may be decreased and the distance between projector 220 and patient 130 may be increased, or the distance between infrared camera 210 and patient 130 may be increased and the distance between projector 220 and patient 130 may be decreased, and thus, the shape of an image may be changed. Therefore, in consideration of the amount of change in distance, the shape of an image to be projected by projector 220 needs to be corrected from an image captured by infrared camera 210.

On the other hand, if the optical paths are the same, even when the position of the subject is changed, a difference in the amount of change between distances to the subject does not occur, because the axes coincide with each other. Therefore, an image can be projected on the basis of the shift correction amount stored in memory 240 without considering the amount of change in distance as in the case where the axes are different from each other. Accordingly, it is preferable that the axis of the optical path of visible laser light 320 and the axis of the optical path of infrared fluorescence 310 are the same.

As presented above, the other exemplary embodiments have been described as an example of the technology according to the present disclosure. For this purpose, the accompanying drawings and the detailed description are provided.

Therefore, components in the accompanying drawings and the detail description may include not only components essential for solving problems, but also components that are provided to illustrate the above described technology and are not essential for solving problems. Therefore, such inessential components should not be readily construed as being essential based on the fact that such inessential components are shown in the accompanying drawings or mentioned in the detailed description.

Further, the above described exemplary embodiments have been described to exemplify the technology according to the present disclosure, and therefore, various modifications, replacements, additions, and omissions may be made within the scope of the claims and the scope of the equivalents thereof.

INDUSTRIAL APPLICABILITY

A projection system according to the present disclosure is applicable to medical application and to the case where work is performed on an object of which state change cannot be confirmed by visual observation in, for example, a construction site, a mining site, a building site, or a material processing plant.

What is claimed is:
1. A projection system comprising:
   a light source that emits first light having a predetermined wavelength to a subject;
   a camera that captures an image of a specific area in the subject, the specific area being specified by second light that is excited by the first light;

a projector that projects the image of the specific area and associated information associated with the image of the specific area by visible light;

a distance sensor that acquires a distance from the distance sensor to the subject by using third light having the predetermined wavelength;

a controller that adjusts a projection magnification in the projector based on the distance, acquired by the distance sensor, from the distance sensor to the subject; and a mirror that causes an optical path of the camera with respect to the subject and an optical path of the projector with respect to the subject to coincide with each other, wherein:

the distance sensor emits the third light in a first period, the light source does not emit the first light in the first period, the controller determines, in the first period, whether the distance acquired by the distance sensor is in a predetermined allowable range, in response to the determining that the distance is in the predetermined allowable range, the controller causes the distance sensor to stop emitting the third light in the first period and causes the light source to emit the first light in a second period, the second period being after the first period, and in response to the determining that the distance is not in the predetermined allowable range, the controller causes the distance sensor to stop emitting the third light in the first period and causes the light source not to emit the first light in the second period.

2. The projection system according to claim 1, wherein the associated information is a line away from the specific area by a predetermined width.

3. The projection system according to claim 1, wherein the associated information is a line enclosing the specific area as being away from the specific area by a predetermined width.

4. The projection system according to claim 1, further comprising a memory that stores a position of the associated information with respect to the specific area.

5. The projection system according to claim 1, wherein the first light is infrared light.

6. The projection system according to claim 1, wherein the associated information is vital data of the subject.

7. The projection system according to claim 1, wherein the projector projects the image in the second period.

8. The projection system according to claim 1, wherein the mirror includes a dichroic mirror.

9. The projection system according to claim 1, wherein the second period is longer than the first period.

10. A projection system comprising:
a light source that emits first light to a subject, the first light being infrared light;
a camera that captures an image of a specific area in the subject, the specific area being specified by second light that is excited by the first light;
a projector that projects the image of the specific area and associated information associated with the image of the specific area by visible light;
a distance sensor that acquires a distance from the distance sensor to the subject by using third light, the third light being infrared light;
a controller that adjusts a projection magnification in the projector based on the distance, acquired by the distance sensor, from the distance sensor to the subject; and
a mirror that causes an optical path of the camera with respect to the subject and an optical path of the projector with respect to the subject to coincide with each other, wherein:
the distance sensor emits the third light in a first period,
the light source does not emit the first light in the first period,
the controller determines, in the first period, whether the distance acquired by the distance sensor is in a predetermined allowable range,
in response to the determining that the distance is in the predetermined allowable range, the controller causes the distance sensor to stop emitting the third light in the first period and causes the light source to emit the first light in a second period, the second period being after the first period, and
in response to the determining that the distance is not in the predetermined allowable range, the controller causes the distance sensor to stop emitting the third light in the first period and causes the light source not to emit the first light in the second period.

11. The projection system according to claim 10, wherein the second period is longer than the first period.

* * * * *